United States Patent
Ferguson et al.

(10) Patent No.: US 11,395,748 B2
(45) Date of Patent: Jul. 26, 2022

(54) DEVICES, SYSTEMS, AND METHODS FOR SOCKET FIT MANAGEMENT

(71) Applicant: U.S. DEPARTMENT OF VETERANS AFFAIRS, Pittsburgh, PA (US)

(72) Inventors: John Ferguson, Minneapolis, MN (US); Gregory Owen Voss, Minneapolis, MN (US); Stuart Richard Fairhurst, Minneapolis, MN (US); Andrew Hansen, Minneapolis, MN (US)

(73) Assignee: United States Government as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/499,998

(22) PCT Filed: Apr. 3, 2018

(86) PCT No.: PCT/US2018/025902
§ 371 (c)(1),
(2) Date: Oct. 1, 2019

(87) PCT Pub. No.: WO2018/187340
PCT Pub. Date: Oct. 11, 2018

(65) Prior Publication Data
US 2020/0060847 A1 Feb. 27, 2020

Related U.S. Application Data

(60) Provisional application No. 62/480,795, filed on Apr. 3, 2017.

(51) Int. Cl.
*A61F 2/80* (2006.01)
*A61B 5/103* (2006.01)
(Continued)

(52) U.S. Cl.
CPC ............... *A61F 2/80* (2013.01); *A61B 5/103* (2013.01); *A61B 5/4851* (2013.01);
(Continued)

(58) Field of Classification Search
CPC ...... A61F 2/80; A61F 2/68; A61F 2/76; A61F 2002/6827; A61F 2002/689;
(Continued)

(56) References Cited

U.S. PATENT DOCUMENTS 7,150,762 B2 12/2006 Caspers
8,308,816 B2 11/2012 Slemker et al.
(Continued)

FOREIGN PATENT DOCUMENTS

CA 3058800 4/2018
EP 18781294.6 4/2018
(Continued)

OTHER PUBLICATIONS

International Search Report and Written Opinion were dated Jun. 25, 2018 by the International Searching Authority for International Application No. PCT/US2018/025902, filed on Apr. 3, 2018 and published as WO/2018/187340 on Oct. 11, 2018 (Applicant—The Government of the United States of America as Represented by the Department of Veterans Affairs) (7 Pages).
(Continued)

*Primary Examiner* — Jerrah Edwards
*Assistant Examiner* — Mihret Tafesse
(74) *Attorney, Agent, or Firm* — Ballard Spahr LLP

(57) ABSTRACT

Disclosed herein are devices, systems, and methods for measuring socket fit in lower limb prostheses and detecting motion of a residual limb relative to a prosthetic socket. Also disclosed herein are methods for developing a socket-fit detection system for sock management that can be applied to adjustable socket systems.

24 Claims, 15 Drawing Sheets

(51) Int. Cl.
*A61B 5/00* (2006.01)
*A61F 2/68* (2006.01)
*A61F 2/76* (2006.01)

(52) U.S. Cl.
CPC .............. *A61B 5/6811* (2013.01); *A61F 2/68* (2013.01); *A61F 2/76* (2013.01); *A61B 2562/0219* (2013.01); *A61B 2562/0247* (2013.01); *A61F 2002/689* (2013.01); *A61F 2002/6827* (2013.01); *A61F 2002/7635* (2013.01)

(58) Field of Classification Search
CPC ........ A61F 2002/7635; A61F 2002/704; A61F 2002/705; A61F 2002/7625; A61F 2002/764; A61F 2002/7655; A61F 2002/769; A61F 2002/7875; A61F 2002/467; A61F 2005/0188; A61B 5/103; A61B 5/4851; A61B 5/6811; A61B 2562/0219; A61B 2562/0247
See application file for complete search history.

(56) References Cited

U.S. PATENT DOCUMENTS

| | | | |
|---|---|---|---|
| 2008/0147204 A1* | 6/2008 | Ezenwa | A61F 2/70 623/33 |
| 2013/0245785 A1 | 9/2013 | Accini et al. | |
| 2015/0216683 A1* | 8/2015 | Laghi | A61F 2/7812 623/36 |
| 2016/0109267 A1* | 4/2016 | Munoz | G01D 5/2291 324/207.18 |

FOREIGN PATENT DOCUMENTS

WO PCT/US2018/025902 4/2018
WO WO-2018/187340 A1 10/2018

OTHER PUBLICATIONS

International Preliminary Report on Patentability was dated Oct. 8, 2019 by the International Searching Authority for International Application No. PCT/US2018/025902, filed on Apr. 3, 2018 and published as WO/2018/187340 on Oct. 11, 2018 (Applicant—The Government of the United States of America as Represented by the Department of Veterans Affairs) (6 Pages).
U.S. Appl. No. 62/480,795, filed Apr. 3, 2017, John Ferguson.

\* cited by examiner

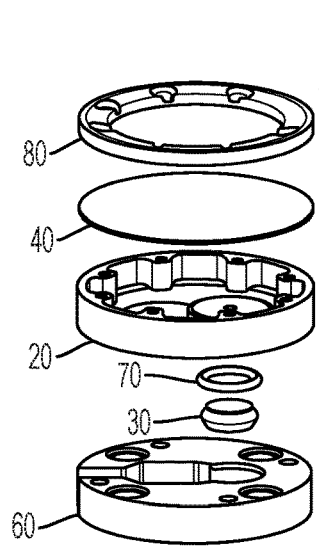
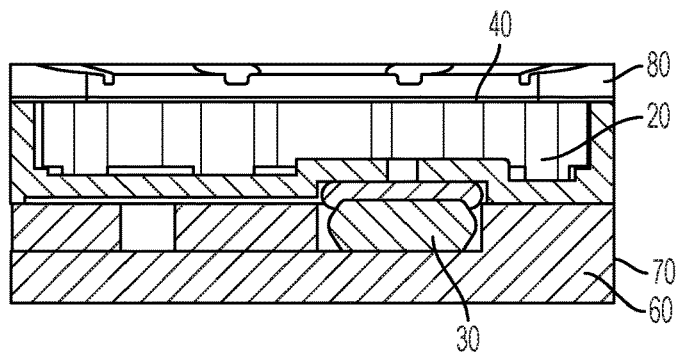
Figure 4B
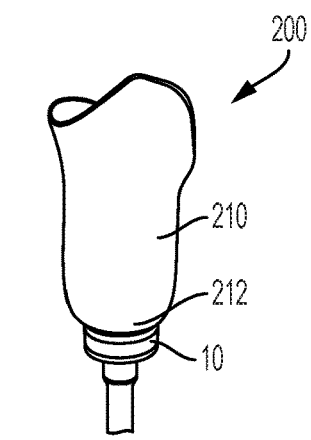
Figure 4A  Figure 4C  Figure 4D
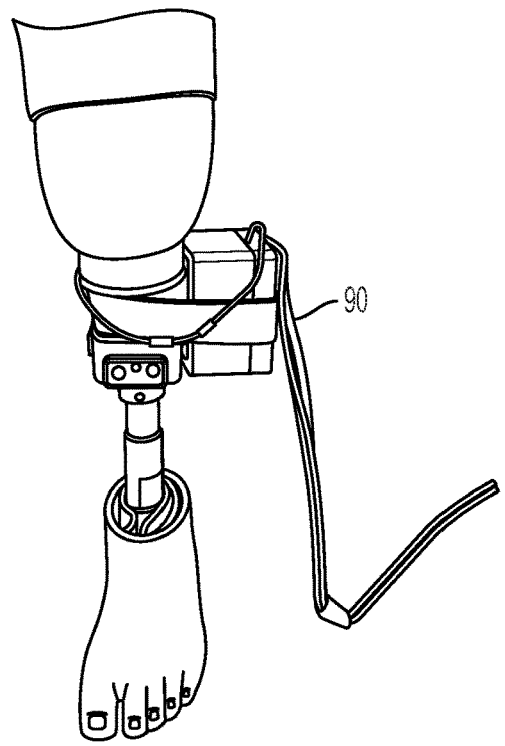
Figure 4E

DEVICES, SYSTEMS, AND METHODS FOR SOCKET FIT MANAGEMENT

CROSS REFERENCE TO RELATED APPLICATIONS

This application is a national stage filing under 35 U.S.C. 371 of International Application No. PCT/US2018/025902, filed on Apr. 3, 2018, which claims the benefit of the filing date of U.S. Provisional Application No. 62/480,795, which was filed on Apr. 3, 2017, the contents of which are incorporated herein by reference in their entireties.

STATEMENT REGARDING FEDERALLY SPONSORED RESEARCH

This invention was made with government support under grant #I21RX002540-01 awarded by the Department of Veterans Affairs, Veterans Health Administration, Office of Research and Development, Rehabilitation Research and Development Service. The government has certain rights in the invention.

BACKGROUND

Many individuals with lower-limb amputations have difficulty knowing when to change sock levels and how much adjustment is necessary, especially if they have poor sensation. Current technologies for measuring socket fit cannot be used for self-management at home.

Thus, there is a need for an easy-to-use, inexpensive device that measures socket fit for individuals with lower-limb amputations for self-management.

SUMMARY

Disclosed herein, in various aspects, is a sensor assembly having a rigid body, a pressure sensor, and a membrane. The rigid body can define an opening extending through a thickness of the rigid body. The pressure sensor can be positioned in fluid communication with the opening of the rigid body. The membrane can be positioned in overlying relation to the rigid body. The rigid body, a lower surface of the membrane, and the pressure sensor can cooperate to define at least a portion of a chamber configured to receive a fluid. The membrane can have an upper surface that is configured for contact with a distal portion of a residual limb of a patient, and the sensor assembly can be configured for complementary receipt within a distal portion of a prosthetic socket. In use, the sensor can be configured to produce an output indicative of changes in pressure within the chamber in response to deformation of the membrane by the distal portion of the residual limb of the patient.

Also disclosed are sensor assemblies configured for use with a prosthesis having a pin-type suspension system.

Further disclosed are systems and methods of using the disclosed sensor assemblies.

Other features and advantages of the present compositions and methods are illustrated in the description below, the drawings, and the claims.

BRIEF DESCRIPTION OF THE DRAWINGS

FIG. 1A is an exploded perspective view of an exemplary sensor assembly as disclosed herein. FIG. 1B is an exploded perspective view of another exemplary sensor assembly as disclosed herein. FIG. 1C is a partial sectional view of the sensor assembly of FIG. 1B, following assembly. FIG. 1D is a close-up sectional view of region 1D labeled in FIG. 1C. FIG. 1E is an exploded perspective view of another exemplary sensor assembly as disclosed herein. FIG. 1F is a partial sectional view of the sensor assembly of FIG. 1E, following assembly. FIG. 1G is a close-up sectional view of region 1G labeled in FIG. 1F.

FIG. 2A is an exploded perspective view of an exemplary sensor assembly as disclosed herein. FIG. 2B is a top view of the sensor assembly of FIG. 2A, following assembly. FIG. 2C is a cross-sectional view of the sensor assembly of FIG. 2B, taken along section line 2C-2C.

FIG. 3A shows a silicon residual limb model. FIGS. 3B-C show a thin force sensor placed in different locations within the socket.

FIGS. 4A-E show images of an exemplary prosthetic socket fit sensing system which has the same form factor as a shuttle lock. FIGS. 4A-B show an exemplary sensor assembly as disclosed herein. FIGS. 4C-D show the socket fit sensing system in a pin suspension system located at the distal end of a lower limb socket. FIG. 4E shows an example of wired connections to processing circuitry, which can be internal and/or external to the sensor assembly.

FIG. 5A shows the results of distal-end pressure and accelerometer data recorded while a subject walked for 15-second trials for each of three different sock conditions: correct socks for a good socket fit (6-ply), too few socks (3-ply), and too many socks (9-ply). FIG. 5B shows that the pressure sensor data was able to differentiate the sock conditions during walking.

DETAILED DESCRIPTION

Figure 1A:
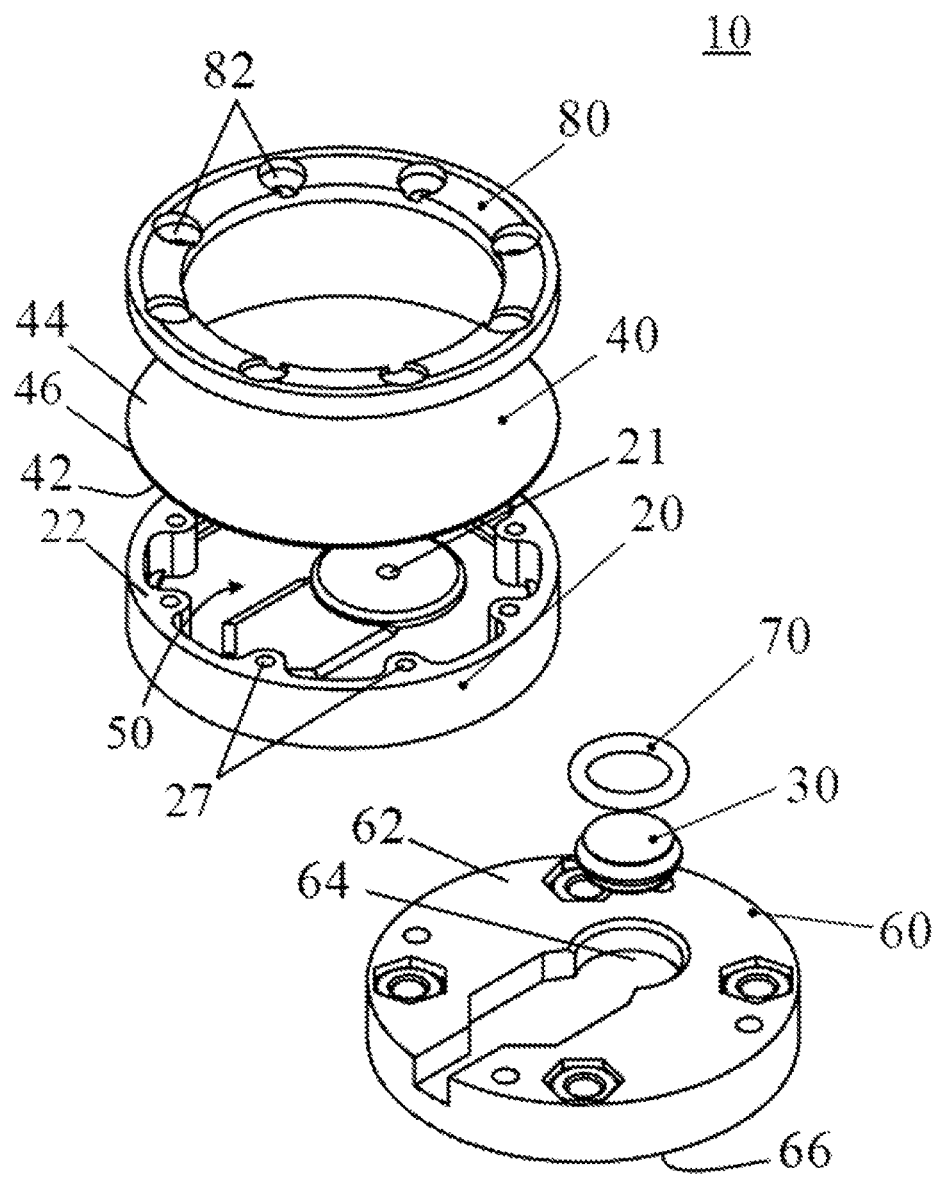
FIGS. 1A-1G depict exemplary sensor assemblies having a membrane, a rigid body, and a lower body as disclosed herein.

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed. Similarly, in some optional aspects, when values are approximated by use of the term "substantially," it is contemplated that values within up to 15%, up to 10%, or up to 5% (above or below) of the particular value can be included within the scope of those aspects.

As used herein, the terms "optional" or "optionally" mean that the subsequently described event or circumstance may or may not occur and that the description includes instances where said event or circumstance occurs and instances where it does not.

As used herein, the term "subject" refers to a human. In some aspects, the subject as described herein can be an individual with one or more lower limb amputations. The term "subject" includes adults, children, adolescents and newborn subjects, whether male or female.

As used herein, the term "patient" refers to a subject afflicted with a lower limb amputation. The term "patient" includes human subjects. In some aspects of the disclosed methods, the "patient" has been diagnosed with a need for treatment, particularly for a prosthesis or sock management.

Introduction

Disclosed herein is a socket-fit sensing and management system for use in the clinic and at home that can adapt to patient-specific changes in limb volume. Further, the device and system described herein can distinguish good sock fit from too many and too few socks. The device design is low cost, easy for prosthetists to build into a socket, and easy for subjects to use on their own. This system can also be used as a training and education tool during post-amputation rehabilitation care in the clinic and as a self-management tool at home.

In current practice, the distal end of a socket contains mechanisms for securing the socket to the rest of the prosthesis. These mechanisms vary depending upon the means of suspension used for holding the socket to the residual limb and include shuttle lock mechanisms for pin suspension and laminated socket attachment blocks.

Although prosthetists build sockets to safely distribute loads, residual limbs frequently change shape and volume over time, which can lead to improper socket fit and potentially injurious interface pressures and shear stresses. Subjects, and in particular, veterans, with lower-limb amputations and clinicians have identified poor socket fit as one of the most significant problems and unmet needs for individuals with amputations. Poor socket fit contributes to skin problems such as ulcers, irritation, inclusion cysts, calluses, and verrucous hyperplasia. In a six-year retrospective chart review, skin problems were found in 40.7% of lower-limb prosthesis users, and problems with the fit of the prosthesis and socks contributed to over 90% of these cases. Additionally, poor socket fit frequently results in discomfort or pain for many veterans. Ultimately, pain, discomfort, or skin problems caused by poor socket fit can lead to reduced prosthesis use, community participation, and quality of life.

To maintain proper socket fit, most individuals with lower-limb amputations are instructed to compensate for changes in limb volume using prosthetic socks. Socks are the most common method of adjusting socket fit because they are inexpensive and effective when used properly. Socks are available in a range of plies and can be combined to obtain a range of thicknesses. Proper sock management involves adding or removing prosthetic socks to offset changes in limb volume. In some instances, a prosthesis user would sense when the prosthesis feels too loose or too tight and respond by adding or removing the appropriate socks.

Although some prosthesis users are able to successfully manage their prosthetic socks or have minimal volume changes and thus do not require daily socket fit adjustments, many prosthesis users have difficulty with sock management. One study of 23 people with transtibial amputations found that socks, on average, were changed less than once per day. Sock management is also challenging for new amputees that are inexperienced and are undergoing volume fluctuations, edema, or muscle atrophy; individuals that have reduced sensation at the residual limb due to peripheral neuropathy; and individuals that have cognitive issues related to dementia or traumatic brain injury. Additionally, many individuals have difficulty with sock management because of the inconvenience of having to stop in the middle of an activity to doff the socket and add or remove socks.

Additionally, every prosthesis user experiences different levels of limb volume fluctuations throughout the day, which may lead to poor socket fit. One study found residual limb volumes changed anywhere between −8.5% per hour and +5.9% per hour during activities, and most individuals decreased limb volume throughout the day while a few increased limb volume throughout the day. The amount of limb volume fluctuation can be affected by the amount of walking, sitting, and standing activities; peripheral artery disease; gender; time since amputation; and prosthesis wear time.

Many individuals with lower-limb amputations have difficulty knowing when to change sock levels and how much adjustment is necessary, especially if they have poor sensation. One study found that clinically unacceptable socket fit occurs at about a 10% volume loss or at a 5.0% volume gain, which corresponds to adding two 5-ply socks or removing one 5-ply sock respectively. However, a different study found that a socket oversized by two 1-ply socks was clinically unacceptable. The complexity of sock management is compounded for prosthesis users because different socks with the same ply may have different thicknesses especially when under load, sock thicknesses change during use, sock plies do not add linearly, and even the act of adding socks can increase the limb volume for some individuals and decrease limb volume for other individuals.

Current technologies for measuring socket fit cannot be used for self-management at home. A range of different technologies have been used to measure variables related to socket fit in research studies, but most of these technologies are not appropriate for use at home. A review of current technology found 26 studies that measured residual limb volume. The methods used to measure residual limb volume included water displacement, casting plus water displacement, anthropomorphic methods, contact probes, optical scanning, ultrasound, computerized tomography, laser scanning, magnetic resonance imaging, and bioimpedance. Another review identified 18 studies that measured pistoning. Pistoning is the motion of the residual limb in the prosthetic socket and is related to prosthetic socket fit. The methods used to measure pistoning included radiography, photography, potentiometers, motion capture, and photoelectric sensors. Of all of these modalities, bioimpedance and photoelectric sensors may be portable enough to be used in a home environment. However, both bioimpedance and photoelectric sensors are in early research stages for prosthetics applications and require more clinical testing and validation and technological developments before they are ready for at-home use by patients.

Strain gauges are too large and power hungry for effective at-home use, while conventional interface pressure sensors are too expensive for home use and difficult for non-clinical users to use/interpret. Thus, there is a need for alternative sensor designs that are capable for in-home measurement of socket fit.

Several adjustable socket systems have been developed that modify socket fit using air-filled bladders or fluid-filled bladders. These systems show promise, but there is limited evidence as to their effectiveness as socket management systems. Prosthetic socks continue to be the primary method of adjusting socket fit for most veterans, due to their low cost and convenience.

As further described below, disclosed herein is a socket fit-detection apparatus that can be used to measure socket fit in lower limb prostheses. The apparatus can be a self-contained sensor assembly 10, 100 designed to fit in the distal end 212 of either a test socket or definitive socket 210, for training or as a permanent indicator, respectively. In exemplary aspects, it is contemplated that the disclosed sensor assemblies 10, 100 can fit in the same space as existing attachment mechanisms, reducing a barrier to acceptance. For example, in one aspect, disclosed sensor assemblies 10, 100 can fit in the distal end 212 of the prosthetic socket 210 and can utilize space used by existing prosthetic components to thereby incorporate current functionality into the system disclosed herein. In use, it is contemplated that the methods disclosed herein for developing a fit-detection system for sock management can also be applied to adjustable socket systems.

Sensor Assemblies

In exemplary aspects, and with reference to FIGS. 1A-2C, the disclosed sensor assemblies 10, 100 can be configured to detect motion of the residual limb relative to the prosthetic socket.

Optionally, in various aspects, and with reference to FIGS. 1A-1G, the sensor assembly 10 can comprise a rigid body 20, a pressure sensor 30, and a membrane 40. In these aspects, the rigid body 20 can define an opening 21 extending through a thickness of the rigid body. The pressure sensor 30 can be positioned in fluid communication with the opening 21 of the rigid body 20, and the membrane 40 can positioned in overlying relation to the rigid body 20. The rigid body 20, a lower surface 42 of the membrane 40, and the pressure sensor 30 can cooperate to define at least a portion of a sealed chamber 50 configured to receive a fluid. The fluid can be capable of transferring force from the membrane to the pressure sensor. In exemplary aspects, the fluid can comprise air or other gas such as nitrogen or argon. Alternatively, it is contemplated that the fluid can be a non-compressible fluid such as silicone-based oil. The membrane 40 can have an upper surface 44 that is configured for contact with a distal portion of a residual limb of a patient. As used herein, it is understood that the term "contact with a distal portion of a residual limb" refers to direct contact with a residual limb of a subject, as well as contact with material covering the distal portion of the residual limb, such as a liner and/or prosthetic socks positioned outside the liner. Thus, in exemplary aspects, the membrane 40 can have an upper surface 44 that is configured for contact with material covering the distal portion of the residual limb of a patient. In exemplary aspects, it is contemplated that the membrane 40 can comprise any elastomeric material, such as, for example and without limitation, any elastomeric material of the classes of non-latex rubber or thermal Plastic elastomers (TPE). Optionally, in these aspects, the membrane 40 can comprise silicone, which is non-reactive, generally hypo allergenic, has an extended shelf life, and can withstand high amounts for strain without tearing. In use, it is contemplated that the strain induced by deflection of the selected material for the membrane 40 can be small such that the resultant force internal to the membrane is small. It is further contemplated that most of the force/pressure generated by contact of the distal end of the residual limb is converted into pressure changes in the fluid-filled chamber rather than internal stress to the membrane.

As further disclosed herein, and with reference to FIGS. 4D-4E, it is contemplated that the sensor assembly 10 can be configured for complementary receipt within a distal portion 212 of a prosthetic socket 210. In use, the pressure sensor 30 can be configured to produce an output indicative of changes in pressure within the chamber 50 in response to deformation of the membrane 40 by the distal portion of the residual limb of the patient. In additional aspects, the sensor assembly 10 can further comprise a lower body 60 that supports the pressure sensor 30 in an operative position and is secured to the rigid body 20. Optionally, in these aspects, it is contemplated that the lower body can be secured to the rigid body by threaded engagement, adhesive, or combinations thereof. Alternatively, it is contemplated that the lower body 60 and the rigid body 20 can be fastened together using a variety of plastic fastening techniques including, for example and without limitation, ultrasonic welding, RF welding, spin welding or a snap fit structure, with complementary structures defined by each component. In further aspects, the lower body 60 can have an upper surface 62 that defines a first receptacle 64 that receives and supports the pressure sensor 30 in the operative position.

In exemplary optional aspects, it is contemplated that the rigid body and the lower body of the sensor assembly 10 can be designed for injection molding from an acrylnitrile-butadiene-styrene (ABS)-polycarbonate (PC) blend. In these aspects, it is contemplated that the design can include, for example, energy directors to facilitate ultrasonic welding assembly of the components into a completed device as further disclosed herein. Although an ABS-PC blend is disclosed as an exemplary material for forming the rigid body and the lower body, it is contemplated that other conventional plastics, including plastics that are configured for injection-molding, can be used.

Optionally, in the operative position, a portion of the pressure sensor 30 can be received within the chamber 50, and the sensor assembly 10 can further comprise a sealing element 70 that forms a seal between the pressure sensor and the rigid body 20 (i.e., the portions of the rigid body surrounding opening 21). In exemplary aspects, the sealing element 70 can be an O-ring.

In further aspects, the membrane 40 can be secured to the rigid body 20. As used herein, unless the context indicates otherwise, the term "secured" does not require direct attachment (such as by a fastener or adhesive); rather, the term "secured to" indicates that the membrane is securely positioned in fixed contact with portions of the rigid body.

In exemplary aspects, and with reference to FIGS. 1A-1G, the rigid body 20 can have a peripheral edge 22, and the membrane 40 can have a peripheral edge portion 46 that covers at least a portion of the peripheral edge of the rigid body. Optionally, in these aspects, and as shown in FIG. 1A, the sensor assembly 10 can further comprise a retaining ring 80 that overlies at least a portion of the peripheral edge portion 46 of the membrane 40 and is secured to the rigid body 20 to retain the membrane in overlying relation to the rigid body. Optionally, it is contemplated that the rigid body 20 and the retaining ring 80 can define respective fastener openings 27, 82 that are configured to receive fasteners to effect secure positioning of the membrane 40 and formation of the chamber 50.

Optionally, in further aspects, and with reference to FIGS. 1B-1G, the rigid body 20 can have an upper body portion 23 and a lower body portion 26 that is inwardly recessed from, and that has a decreased diameter relative to, the upper body portion. In these aspects, it is contemplated that the upper body portion 23 of the rigid body 20 can comprise a circumferential flange 24 that defines the peripheral edge 22 of the rigid body. In further exemplary aspects, it is contemplated that the circumferential flange 24 of the rigid body 20 can have a variable height that increases moving toward the peripheral edge 22 of the rigid body, thereby producing a desired vertical separation between the membrane 40 and the rigid body to form the chamber 50.

Figure 1B:
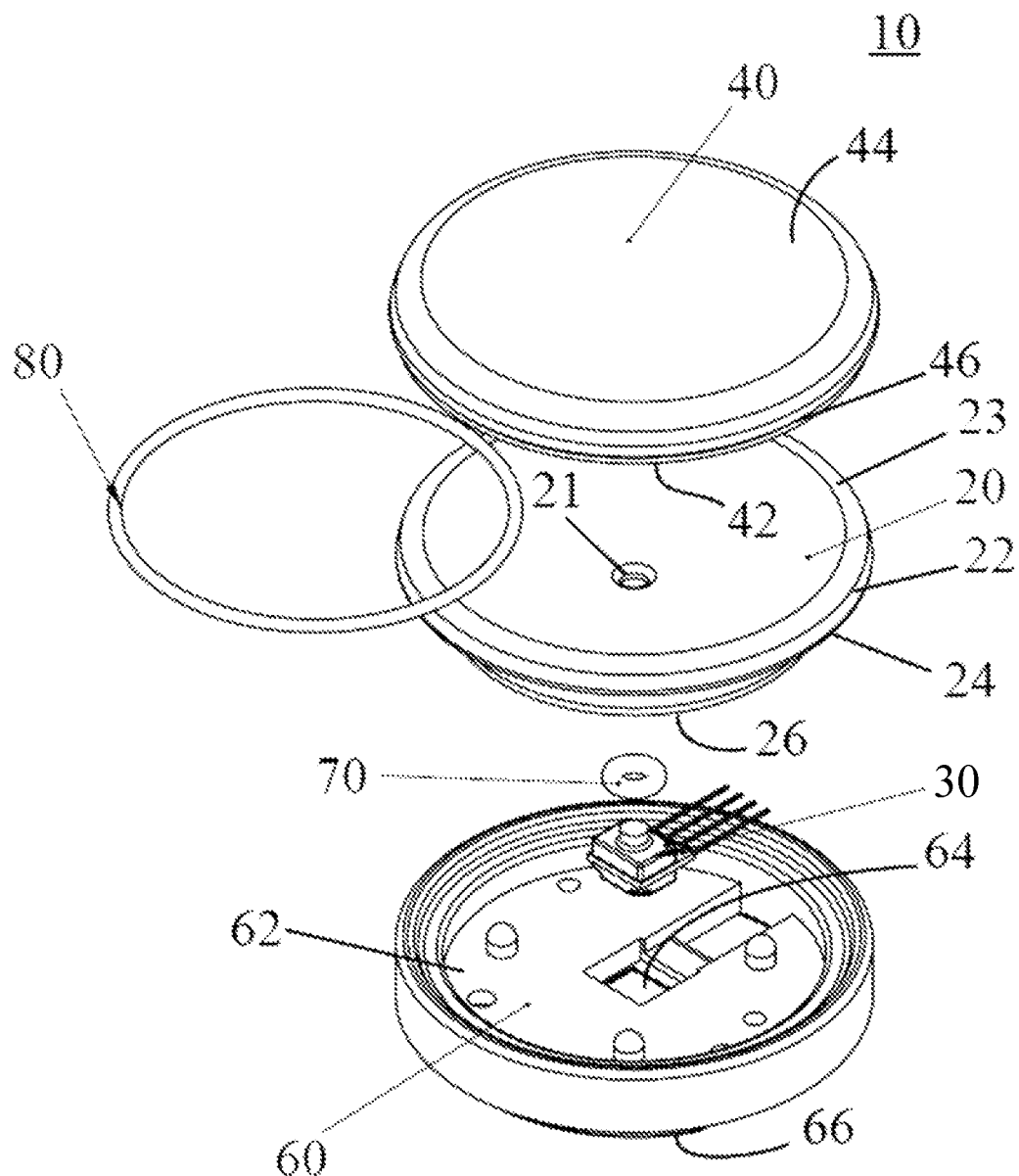
Figure 1C:
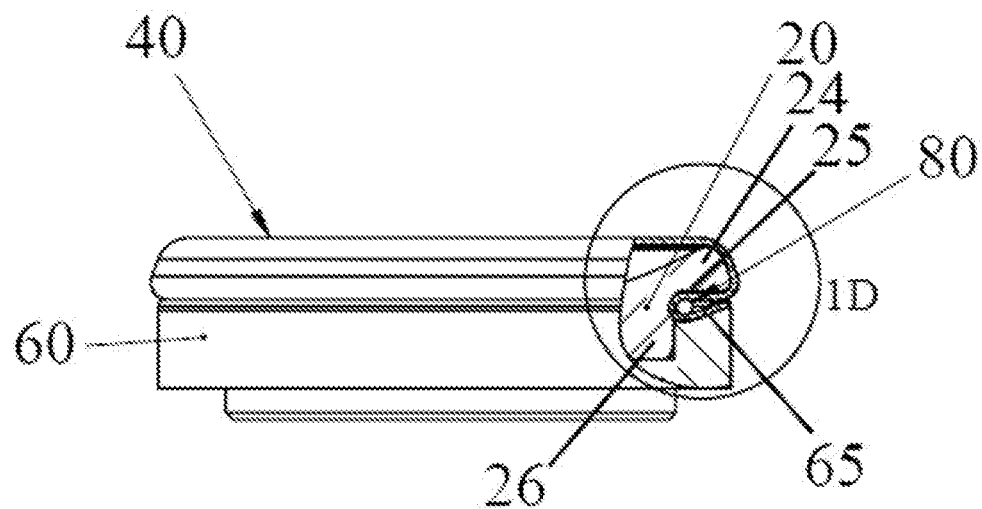
Figure 1D:
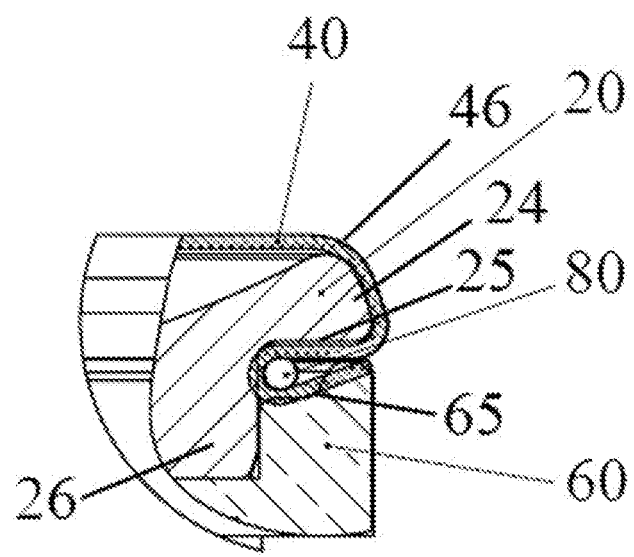

In exemplary aspects, and with reference to FIGS. 1B-1D, the circumferential flange 24 of the upper body portion 23 can have a lower surface 25 extending between the lower body portion 26 and the peripheral edge 22 of the rigid body 20. In these aspects, it is contemplated that at least a portion of the peripheral edge portion 46 of the membrane 40 can engage the lower surface of the circumferential flange. In further aspects, the sensor assembly 10 can comprise a retaining ring 80 that secures the membrane to the lower surface of the circumferential flange of the upper body portion of the rigid body. In these aspects, it is contemplated that the retaining ring 80 can be an O-ring having a complementary shape and diameter to the lower body portion 26 of the rigid body 20 as shown in FIGS. 1C-1D. Thus, when forming the sensor assembly disclosed in FIGS. 1B-1D, the membrane 40 can be wrapped over the top of the rigid body and fastened underneath using the retaining ring 80. As shown, the circumferential flange 24 of the rigid body 20 can define a smooth transition surface with no sharp edges that can lead to tissue irritation. Thus, when the membrane is wrapped over the circumferential flange 24 of the rigid body, the smooth outer surface of the sensor assembly is preserved. In particular, as shown in FIG. 1D, the membrane 40 can be wrapped above and around the circumferential flange 24 of the rigid body, forming the fluid filled chamber 50. The membrane 40 can then wrap underneath the circumferential flange 24, around the retaining ring 80, and back out to an outside edge of the lower body 60. The lower body 60 can be secured or fastened to the rigid body 20 to squeeze and seal the retaining ring 80 and the membrane 40 to the lower surface 25 of the circumferential flange 24 to create the fluid filled chamber.

In contrast to the sensor assembly depicted in FIG. 1A, it is understood that the sensor assembly depicted in FIGS. 1B-1D can allow the membrane 40 to be secured to the rigid body 20 without the use of an upper fastening ring. Although the opening 21 within the rigid body is shown in a particular centralized position, it is understood that other suitable positions for the opening 21 can be used. In particular, it should be understood that the opening 21 need not be centrally located at a center point of the rigid body 20.

Figure 1E:
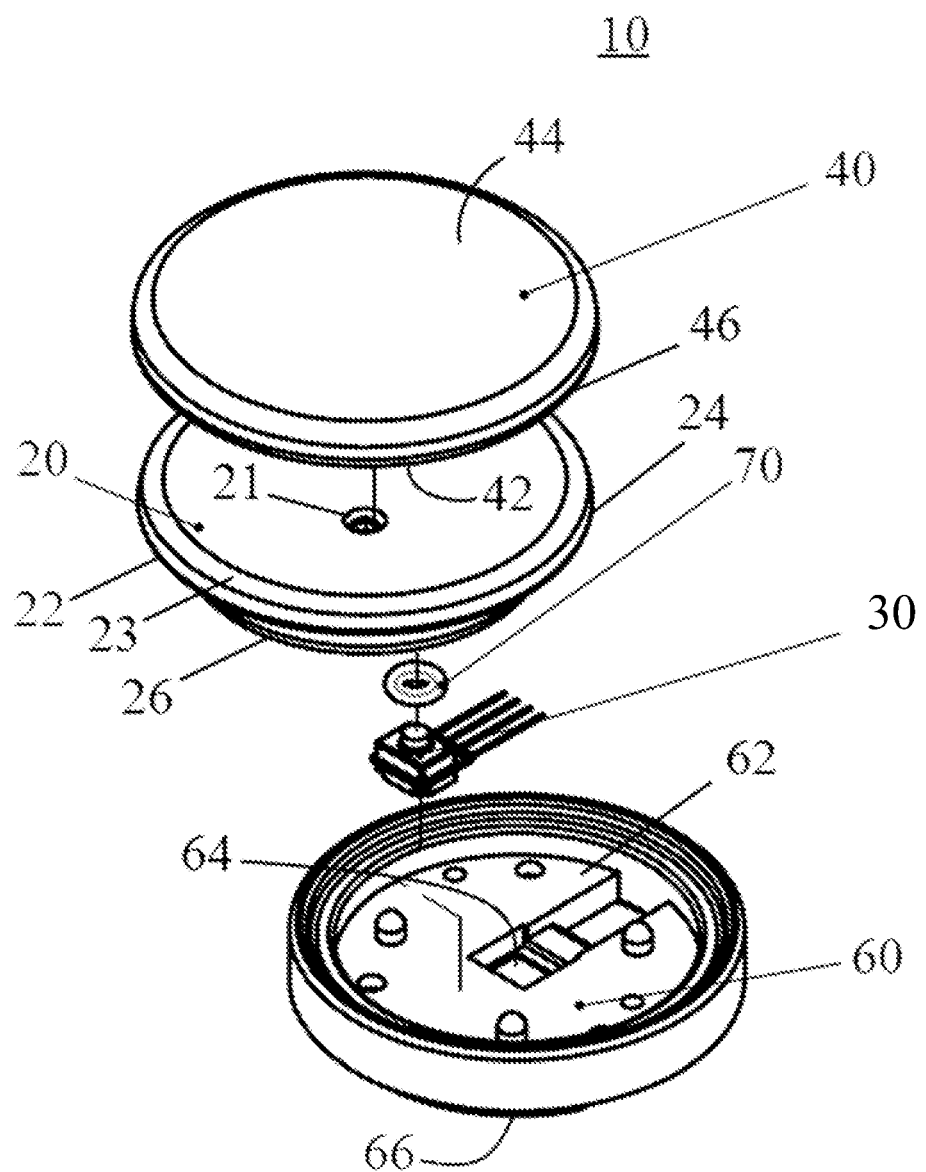
Figure 1F:
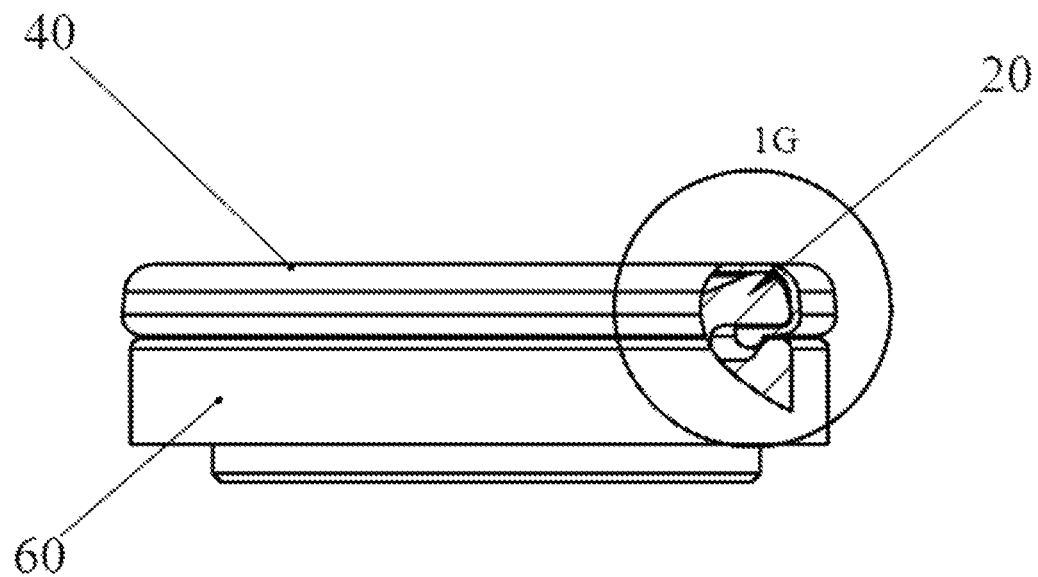
Figure 1G:
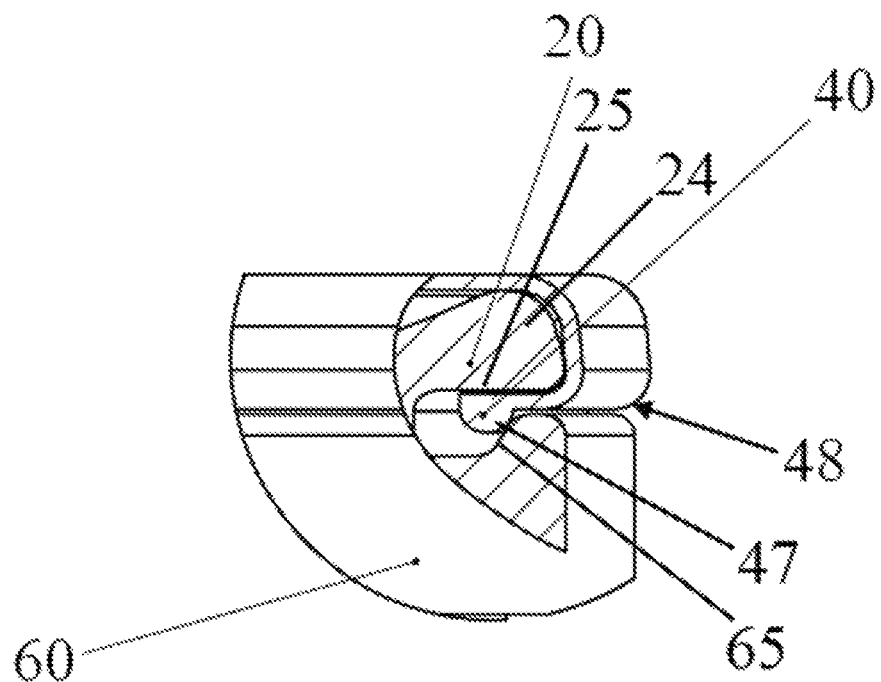

Optionally, in further aspects, and with reference to FIGS. 1E-1G, it is contemplated that the membrane 40 can be molded with an undercut portion 48 that is complementary to the shape of the circumferential flange 24 of the upper body portion 23 of the rigid body 20. In these aspects, it is contemplated that the peripheral edge portion 46 of the molded membrane 40 can define a circumferential projection 47 that is configured to frictionally engage a portion of the lower body (e.g., engagement surface 65). During assembly, it is contemplated that the undercut portion 48 of the molded membrane 40 can allow the membrane to wrap around the circumferential flange 24 of the rigid frame. Additionally, it is contemplated that the circumferential projection 47 of the molded membrane 40 can provided a section of increased thickness that allows the membrane to be captured and held in position through engagement with the engagement surface 65 of the lower body 60. As shown, the circumferential flange 24 of the rigid body 20 can define a smooth transition surface with no sharp edges that can lead to tissue irritation. Thus, when the membrane is wrapped over the circumferential flange 24 of the rigid body, the smooth outer surface of the sensor assembly is preserved. In particular, as shown in FIG. 1G, the membrane 40 can wrapping above and around the circumferential flange 24 of the rigid body 20, thereby forming the fluid filled chamber 50. The membrane 40 can wrap underneath the circumferential flange 24, and the circumferential projection 47 of the molded membrane can engage the engagement surface 65 of the lower body 60 to hold the membrane in position. It is contemplated that the circumferential projection 47 that is molded into the membrane 40 can be resilient to permit compression and creation of a liquid tight seal. The lower body 60 can be secured or fastened to the rigid body 20 to squeeze and seal the projection 47 to the lower surface 25 of the circumferential flange 24 of the rigid body 20, thereby creating the fluid filled chamber 50.

In contrast to the sensor assembly depicted in FIG. 1A, it is understood that the sensor assembly depicted in FIGS. 1E-1G can allow the membrane 40 to be secured to the rigid body 20 without the use of an upper fastening ring. Although the opening 21 within the rigid body is shown in a particular centralized position, it is understood that other suitable positions for the opening 21 can be used. In particular, it should be understood that the opening 21 need not be centrally located at a center point of the rigid body 20.

Figure 2A:
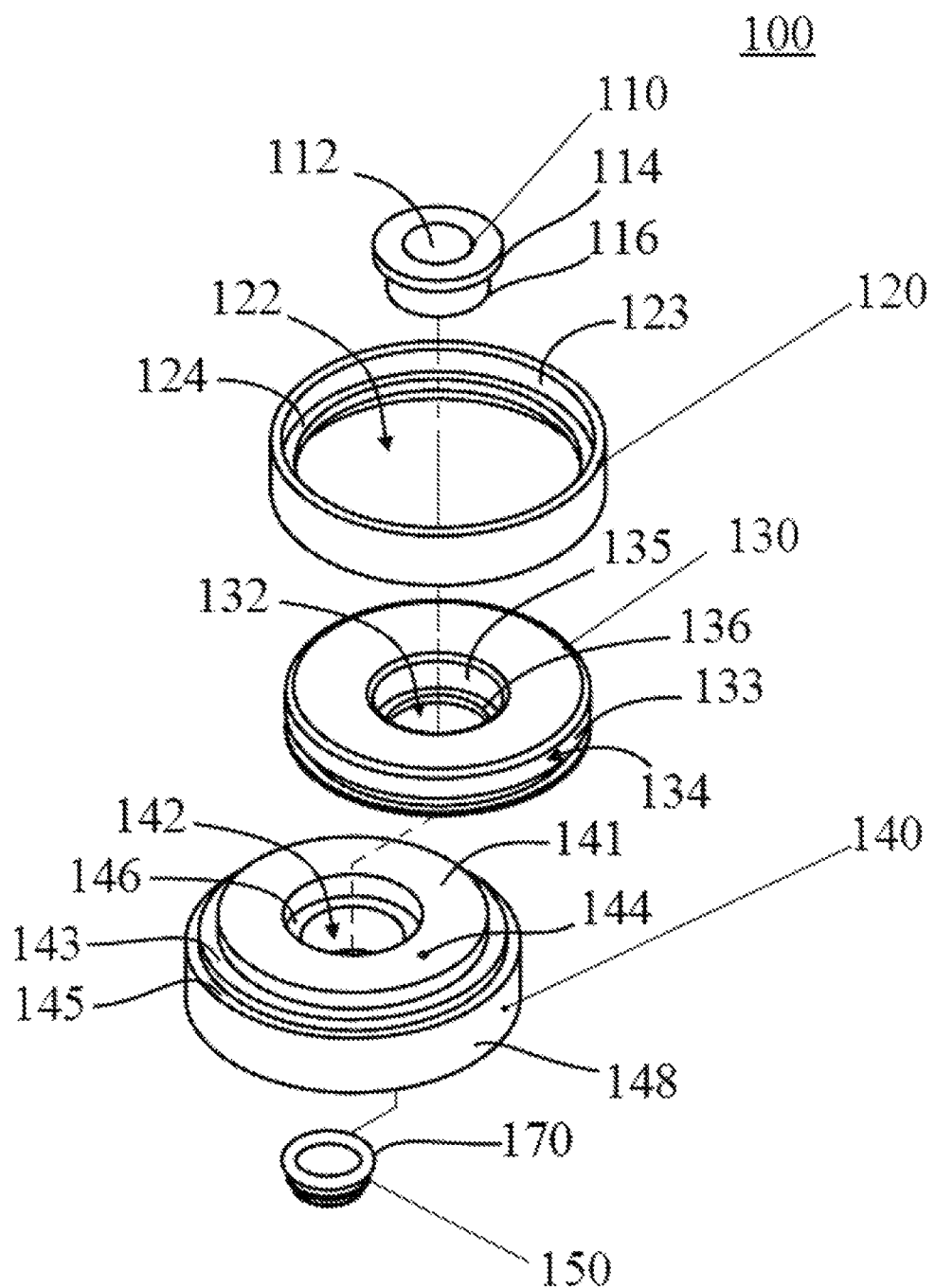
FIGS. 2A-2C depict an exemplary sensor assembly for use with a prosthesis having a pin suspension design.
Figure 2B:
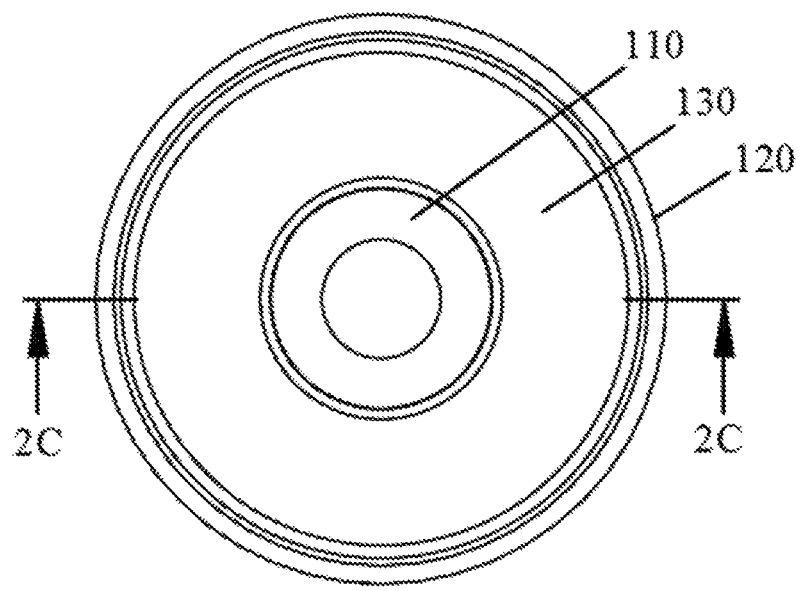
Figure 2C:
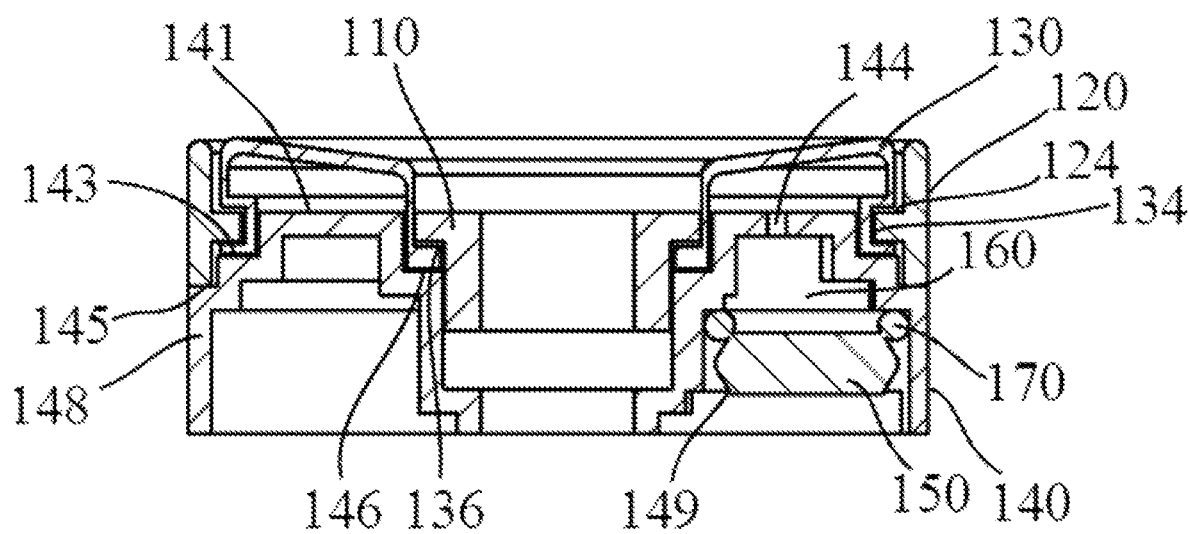

In further exemplary aspects, and with reference to FIGS. 2A-2C, a sensor assembly 100 for use with prostheses having a pin-type suspension system is disclosed. Pin suspension systems use a metal pin attached to a flexible liner worn by the patient. The pin protrudes out the distal end of the flexible liner and can be inserted into a locking mechanism at the distal end of the socket called a shuttle lock. In exemplary aspects, the sensory assembly 100 can comprise an inner fastening ring 110, an outer fastening ring 120, a diaphragm 130, a rigid body 140, and a pressure sensor 150. In these aspects, the inner fastening ring 110, the outer fastening ring 120, the diaphragm 130, and the rigid body 140 can define respective central openings 112, 122, 132, 142 that are configured to cooperate to define a central through-opening that is configured to receive a pin of a suspension system as is known in the art. As one can appreciate, the presence of such a pin can preclude the use of a membrane of the type shown in FIGS. 1A-1G.

Like membrane 40, diaphragm 130 can have an upper surface that is configured for contact with material covering the distal portion of the residual limb of a patient. In exemplary aspects, it is contemplated that the diaphragm 130 can comprise any elastomeric material, such as, for example and without limitation, any elastomeric material of the classes of non-latex rubber or thermal Plastic elastomers (TPE). Optionally, in these aspects, the diaphragm can comprise silicone, which is non-reactive, generally hypo allergenic, has an extended shelf life, and can withstand high amounts for strain without tearing. In use, it is contemplated that the strain induced by deflection of the selected material for the diaphragm can be small such that the resultant force internal to the diaphragm is small. It is further contemplated that most of the force/pressure generated by contact of the distal end of the residual limb is converted into pressure changes in the fluid-filled chamber as disclosed herein rather than internal stress to the diaphragm.

In exemplary aspects, the rigid body 140 can define a receptacle 149 that receives the pressure sensor 150. As shown in FIG. 2C, within the receptacle 149, the pressure sensor 150 can be positioned in fluid communication with a fluid opening 144 defined in an upper surface 141 of the rigid body 140. A sealing element 170 (e.g., an O-ring) can cooperate with the pressure sensor 150 and interior surfaces of the receptacle 149 to form a fluid tight seal.

The rigid body 140 can define a ledge 146 proximate the central opening 142 of the rigid body and first and second circumferential steps 143, 145 proximate an outer surface of the rigid body. The first circumferential step 143 can extend downwardly from the upper surface 141 of the rigid body 140, and the second circumferential step 145 can extend downwardly from the first circumferential step and radially outwardly to the outer surface of the rigid body. The ledge 146 and the first circumferential step 143 can be configured to engage corresponding portions of a bottom surface of the diaphragm as the diaphragm is positioned over the upper surface 141 of the rigid body 140. As shown in FIG. 2C, it is contemplated that the diaphragm 130 can have a recessed portion that is configured to receive a portion of the rigid body that projects upwardly (from first circumferential step 143) to define the upper surface 141. Additionally, it is contemplated that the diaphragm 130 can have an outer surface 133 that defines an outer slot 134 and an inner surface 135 that defines a seat 136 for engagement with the inner fastening ring 110 as further disclosed herein.

With the diaphragm 130 positioned over the rigid body, the outer fastening ring 120 can secure the diaphragm against the rigid body. As shown in FIGS. 2A and 2C, the outer fastening ring 120 can have an interior surface 123 that defines a projection 124 that is configured for receipt within the outer slot 134 defined by the diaphragm 130. In exemplary aspects, the outer fastening ring 120 can be positioned circumferentially around the diaphragm 130 such that the projection 124 is received within and engages the outer slot 134 of the diaphragm, and a bottom surface of the outer fastening ring can be supported by a second step 145 defined by the rigid body. In this position, the projection 124 of the outer fastening ring can secure the diaphragm 130 against the rigid body 140 as shown in FIG. 2C, thereby forming a fluid tight seal. It is further contemplated that the projection 124 of the outer fastening ring 120 can be complementary in shape to the steps 143, 145 defined by the rigid body. Optionally, it is contemplated that the rigid body 140 can have a lower body portion 148 having the same or substantially the same operative diameter of the outer fastening ring 120 (following assembly), thereby providing a smooth outer surface for the sensor assembly 100.

In further aspects, as shown in FIG. 2A, the inner fastening ring 110 can have an upper flange portion 114 and a lower portion 116 that is recessed relative to the upper flange portion. In these aspects, it is contemplated that the inner fastening ring 110 can be received within the common central opening defined by the rigid body 140 and the diaphragm 130. As the inner fastening ring 110 is received within the common central opening, the upper flange portion 114 of the inner fastening ring contacts the seat 136 defined by the diaphragm, thereby preventing further advancement of the inner fastening ring and reinforcing the fluid seal between the diaphragm and the rigid body.

In use, it is contemplated that a fluid can be provided within chamber 160, which can include an interior space within the diaphragm, the fluid opening 144, and a space between the fluid opening 144 and the pressure sensor 150. In exemplary aspects, the fluid can comprise air or other gas such as nitrogen or argon. Alternatively, it is contemplated that the fluid can be a non-compressible fluid such as silicone-based oil. As force is applied to the diaphragm, the diaphragm can be deformed, and pressure changes within chamber 160 can be detected by the pressure sensor 150.

Figure 6:
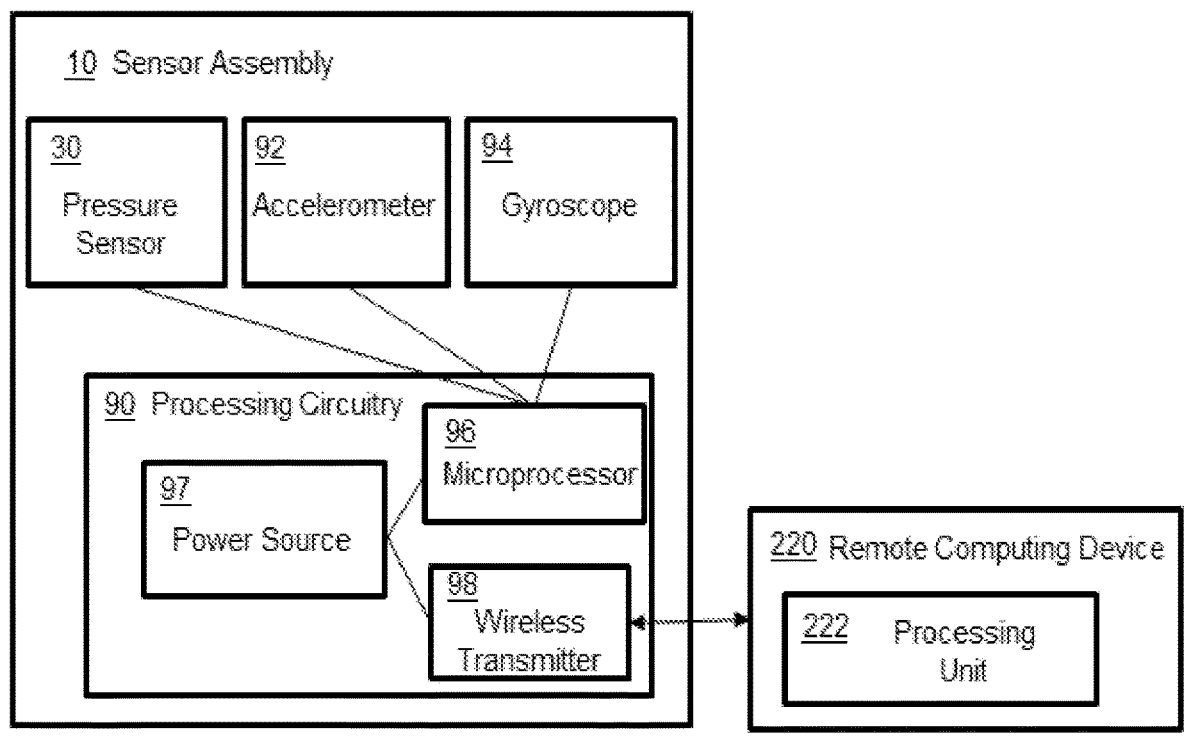
FIG. 6 is a schematic diagram depicting an exemplary configuration of a socket fit management system as disclosed herein. As shown, it is contemplated that the processing circuitry of the sensor assemblies disclosed herein can be communicatively coupled to a remote computing device.
Figure 7A:
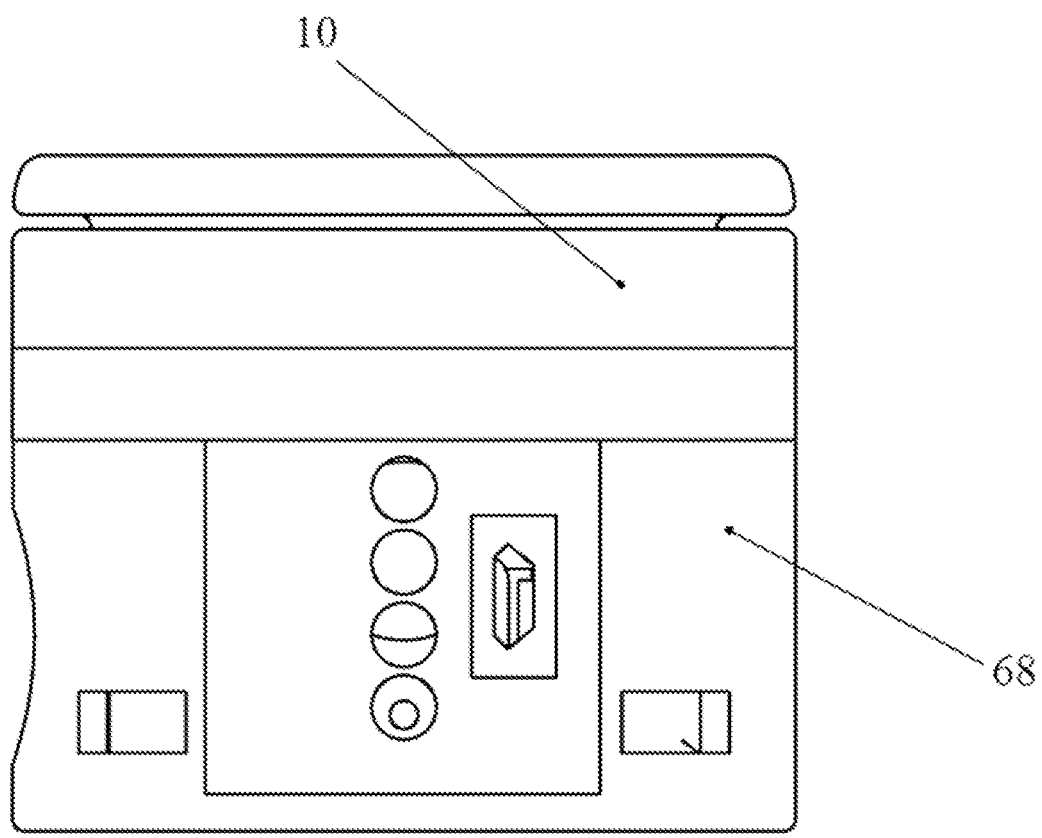
FIG. 7A is a side view of an assembled sensing assembly as disclosed herein, showing a second receptacle attached to the sensing assembly.
Figure 7B:
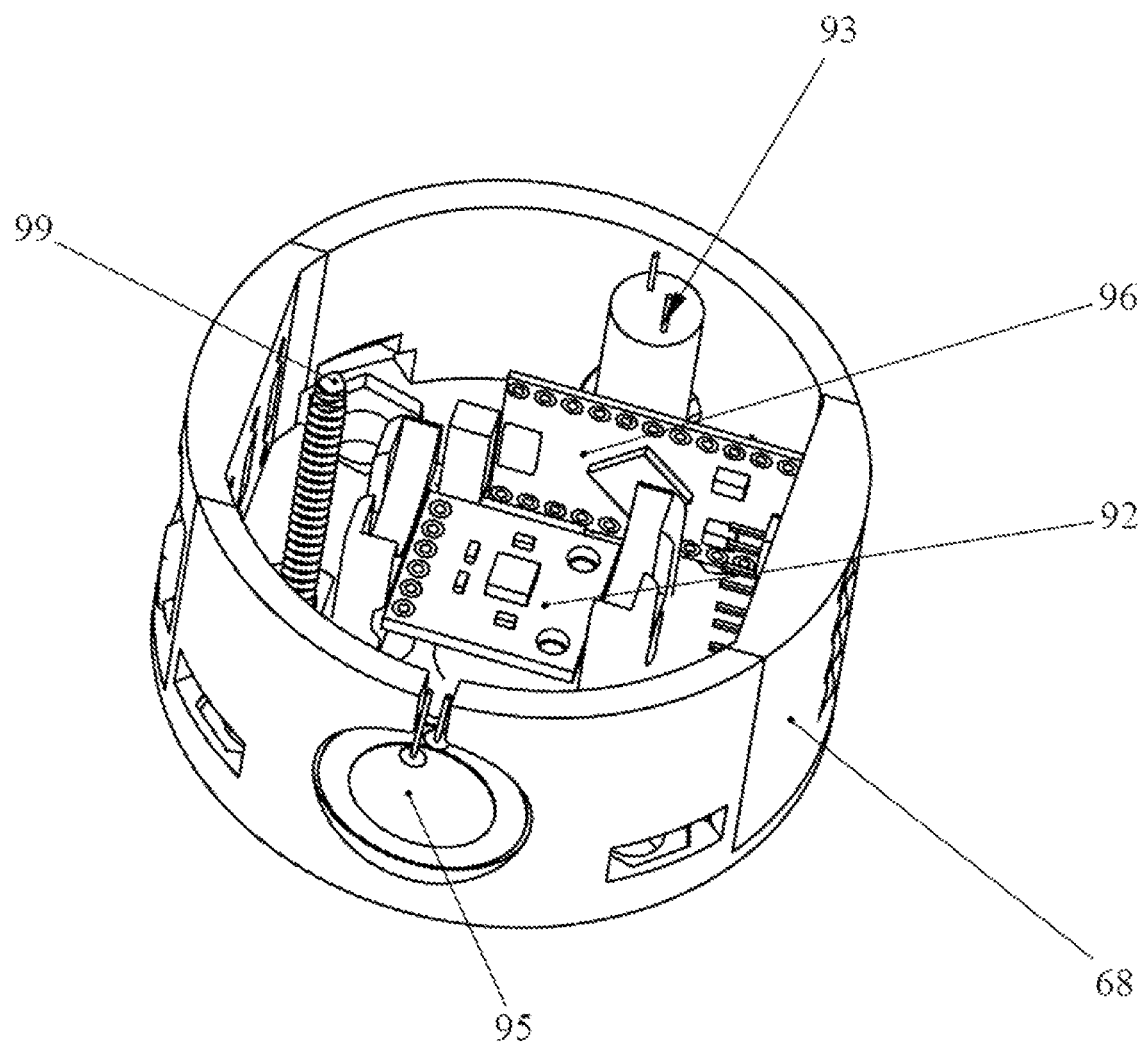
FIG. 7B is an isolated top perspective view depicting an exemplary second receptacle for housing processing circuitry as disclosed herein.

In exemplary aspects, and with reference to FIG. 6, the sensor assembly 10, 100 can further comprise processing circuitry 90 that is communicatively coupled to the pressure sensor 30. Optionally, in these aspects, and with reference to FIG. 7A, in addition to having a first receptacle 64 in the upper surface of the lower body 60 that receives the pressure sensor 30, it is contemplated that the lower body 60 can have a lower surface 66 that is configured for engagement with a second receptacle 68 that is configured to receive at least a portion of the processing circuitry 90. As shown in FIG. 7B, the second receptacle 68 can be secured to the lower body 60 using a fastener 99. As further described herein, and as depicted in FIG. 7B, it is contemplated that the second receptacle can cooperate with the lower body to at least partially enclose a microcontroller 96, an accelerometer 92, a vibratory feedback element 93, and an auditory feedback element 95.

In exemplary aspects, and with reference to FIG. 6, it is contemplated that the processing circuitry 90 of the sensor assembly 10, 100 can optionally comprise a microprocessor 96 (e.g., a microcontroller), a power source 97 (e.g., a rechargeable power source), and a wireless transmitter 98 or other communication module for processing and reporting on a quality of sock fit. It is further contemplated that the processing circuitry 90 can optionally comprise a memory (not shown) that is positioned in communication with the microcontroller 96 and configured to store software or data for use in on-board processing. In further exemplary aspects, the second receptacle can be configured to house Intel Edison or other ultra-small computing platform designed for Internet of Things (IoT) applications. It is contemplated that such processing circuitry can include, for example, a dual-core Central Processing Unit (CPU) and single core microcontroller, have integrated Wi-Fi and Bluetooth support, and run on a battery for at least a day between charges.

Optionally, in further exemplary aspects, and with reference to FIGS. 6 and 7B, the sensor assembly 10, 100 can further comprise an accelerometer 92 that is communicatively coupled to the processing circuitry 90. Additionally, or alternatively, in further exemplary aspects, it is contemplated that the sensor assembly can further comprise a gyroscope 94 (e.g., a three-axis gyroscope) that is communicatively coupled to the processing circuitry. Additionally, or alternatively, it is contemplated that the sensor assembly can further comprise a magnetometer (not shown) that is communicatively coupled to the processing circuitry of the sensor assembly. In further exemplary aspects, it is contemplated that the sensor assembly can further comprise a 6-axis inertial measurement unit (IMU) that is communicatively coupled to the processing circuitry. In other exemplary aspects, it is contemplated that an accelerometer, a gyroscope 94, and a magnetometer can be provided together as a 9-degree-of-freedom accelerometer-magnetometer-gyroscope. In use, it is contemplated that the disclosed accelerometer 92, gyroscope 94, and magnetometer can be used alone or in combination to produce outputs that are indicative of movement patterns of a patient, including for example and without limitation, standing, swaying, and walking.

In further aspects, a socket fit management system 200 can be provided. In these aspects, in addition to a sensor assembly 10, 100 as disclosed herein, the system 200 can include a prosthetic socket 210 having a distal portion 212 as further disclosed herein. In exemplary aspects, the sensor assembly can be received within the distal portion of the prosthetic socket.

In exemplary aspects, and as further disclosed herein, the sensor assembly 10, 100 can comprise processing circuitry 90 that is communicatively coupled to the pressure sensor 30.

In still further aspects, it is contemplated that the sensor assembly 10, 100 can comprise components that are capable of generating visual, audible, or vibrational outputs that are detectable by a user. For example, in exemplary aspects, the processing circuitry 90 of the sensor assembly 10, 100 can further comprise a vibrational motor or other vibratory feedback element 93 that is configured to generate vibration at a selected pattern or sequence to indicate particular characteristics of measured socket fit. For example, and without limitations, it is contemplated that a number of vibrations per burst of vibrations, a number of vibrations per second, or a duration of a burst of vibrations can be used to indicate particular conditions. Additionally, or alternatively, in other exemplary aspects, the processing circuitry of the sensor assembly 10, 100 can be communicatively coupled to at least one visual output element such as at least one light-emitting diode (LED), which can be used to provide a visual indication corresponding to particular characteristics of measured socket fit. Additionally, or alternatively, in other exemplary aspects, the processing circuitry of the sensor assembly 10, 100 can be communicatively coupled to at least one auditory feedback element 95 such as a speaker and sound generating hardware as is known in the art, which can be used to provide an audible indication corresponding to particular characteristics of measured socket fit.

Optionally, in additional aspects, and with reference to FIG. 6, the socket fit management system 200 can further comprise a remote computing device 220 that is communicatively coupled to the processing circuitry 90 of the sensor assembly 10, 100. In exemplary aspects, it is contemplated that the processing circuitry 90 of the sensor assembly 10, 100 can comprise a wireless transmitter (e.g., a Bluetooth-enabled radio or other wireless radio) 98 that is configured to transmit data from the processing circuitry 90 to the remote computing device 220. Exemplary remote computing devices 220 include computers, smartphones, tablets, and the like. In some exemplary aspects, and as further disclosed herein, the remote computing device 220 can have a processing unit 222 that is configured to analyze (e.g., configured to run software that analyzes) the information (e.g., data) received from the processing circuitry to produce an output indicative of the quality of socket fit for a patient.

In use, it is contemplated that the disclosed sensor assembly 10, 100 and the disclosed socket fit management system 200 can measure changes in pressure resulting from movement of a residual limb having a distal portion (or covering materials placed over the distal portion) in contact with an upper surface of the membrane of the sensor assembly. In exemplary aspects, based upon the outputs received from the sensing elements disclosed herein, the processing circuitry of the sensor assembly can be configured to determine a quality of fit between the residual limb and a socket within which the sensor assembly is positioned. In further exemplary aspects, the disclosed methods can include remotely transmitting data indicative of the quality of fit between the residual limb and the socket from the processing circuitry of the sensor assembly to a remote computing device. In still further exemplary aspects, when the sensor assembly further comprises an accelerometer, a gyroscope, and/or a magnetometer that is communicatively coupled to the processing circuitry of the sensor assembly, the accelerometer, the gyroscope, and/or the magnetometer can produce an output (or respective outputs) indicative of a type of movement of the patient. In combination with the measured pressure data, it is contemplated that the acceleration, directional, and/or magnetic data received from the disclosed sensors can provide context to the recorded pressure data. For example, it is contemplated that the acceleration data can provide information concerning the type movement of the patient (sitting, standing, swaying, and the like) while also allowing for extrapolation of usage information and gait information.

As further disclosed herein, the processing circuitry of sensor assembly 10, 100 can be connected to the pressure sensor and to the accelerometer and/or other sensors (e.g., breakout boards that contain a 9-degree-of-freedom accelerometer-magnetometer-gyroscope). Optionally, the processing circuitry can be used to control several Light Emitting Diodes (LEDs). Additionally, or alternatively, as depicted in FIG. 7B, it is contemplated that the processing circuitry 90 can comprise at least one vibratory feedback element 93 (e.g., a vibrating motor) and/or at least one auditory feedback element 95 (e.g., a speaker and associated sound generating hardware). In use, it is contemplated that the disclosed vibratory feedback element 93 can be configured to produce a vibrational output in response to detection of an alarm condition, such as a poor quality fit or detection of dangerous movement. It is further contemplated that different vibrational outputs can correspond to different conditions detected by the disclosed sensor assembly. Similarly, it is contemplated that the disclosed auditory feedback element 95 can be configured to produce an audible output in response to detection of an alarm condition, such as a poor quality fit or detection of dangerous movement. It is still further contemplated that different audible outputs can correspond to different conditions detected by the disclosed sensor assembly. Optionally, the disclosed process circuitry (e.g., Edison) can run Yocto Linux and support Python and Node.js software development. It is contemplated that Python and the "scikit-learn" Python machine learning library can be used to create a platform for developing socket-fit detection algorithms that can be tested. It is contemplated that Node.js can be used to create a "clinician interface" on a separate computer or remote computing (e.g., mobile) device, which can be connected wirelessly by Bluetooth or using a micro-Universal Serial Bus (USB) cable. It is contemplated that this clinician interface can allow a physical therapist (PT), prosthetist, physiatrist, or researcher to adjust device settings, control the socket-fit detection algorithm, and to view detailed information from the sensors (including walking data, socket wear data, and socket fit data).

It is contemplated that use of a membrane-covered pressure system for motion detection as disclosed herein can be insensitive to problems encountered by other types of force or displacement detection systems including, but not limited to mechanical friction in moving components or loading anomalies caused by off axis loading or shape changes in the residual limb.

Importantly, the devices, systems, and methods disclosed herein can allow for recording movement within a socket without the need for multiple sensors or the presence of a hard surface, which is not conducive to everyday use with living tissue as is present in a residual limb. Additionally, it is contemplated that the disclosed devices, systems, and methods can be effective without requiring precise positioning of a load applied by the residual limb of the subject. Further, it is contemplated that the disclosed devices, systems, and methods can be used in any circumstances while also providing easier fabrication and easier use in comparison with current socket-fit monitoring devices.

EXAMPLES

Figure 3C:
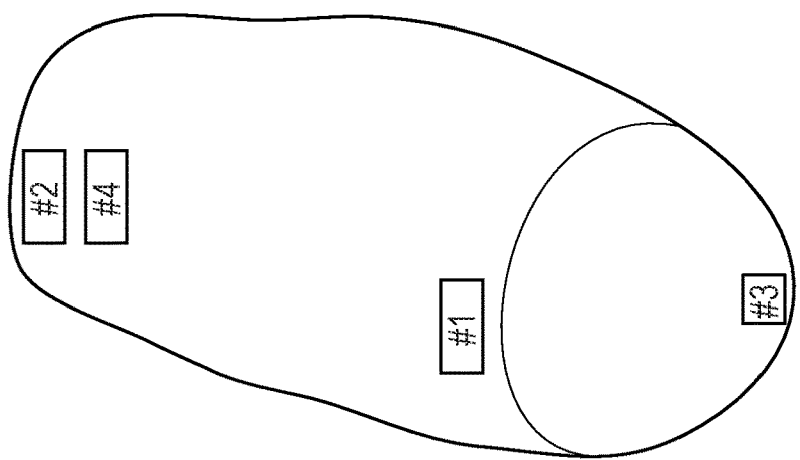
FIGS. 3A-C show images (FIGS. 3A-C) of sockets based on results (FIG. 3D) on simulated standing tests.
Figure 3B:
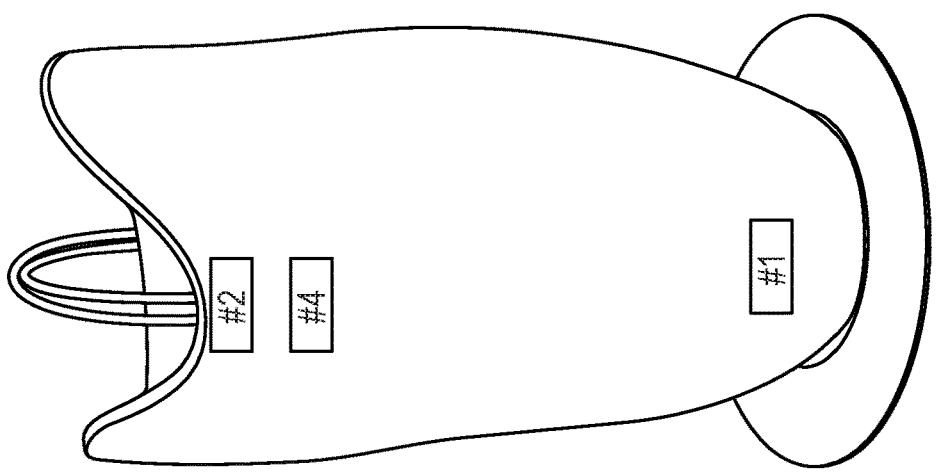
Figure 3A:
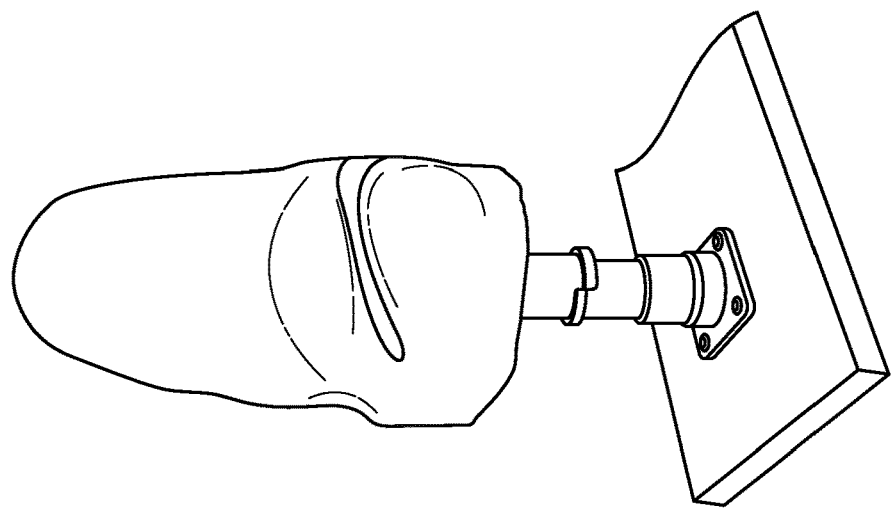
Figure 3D:
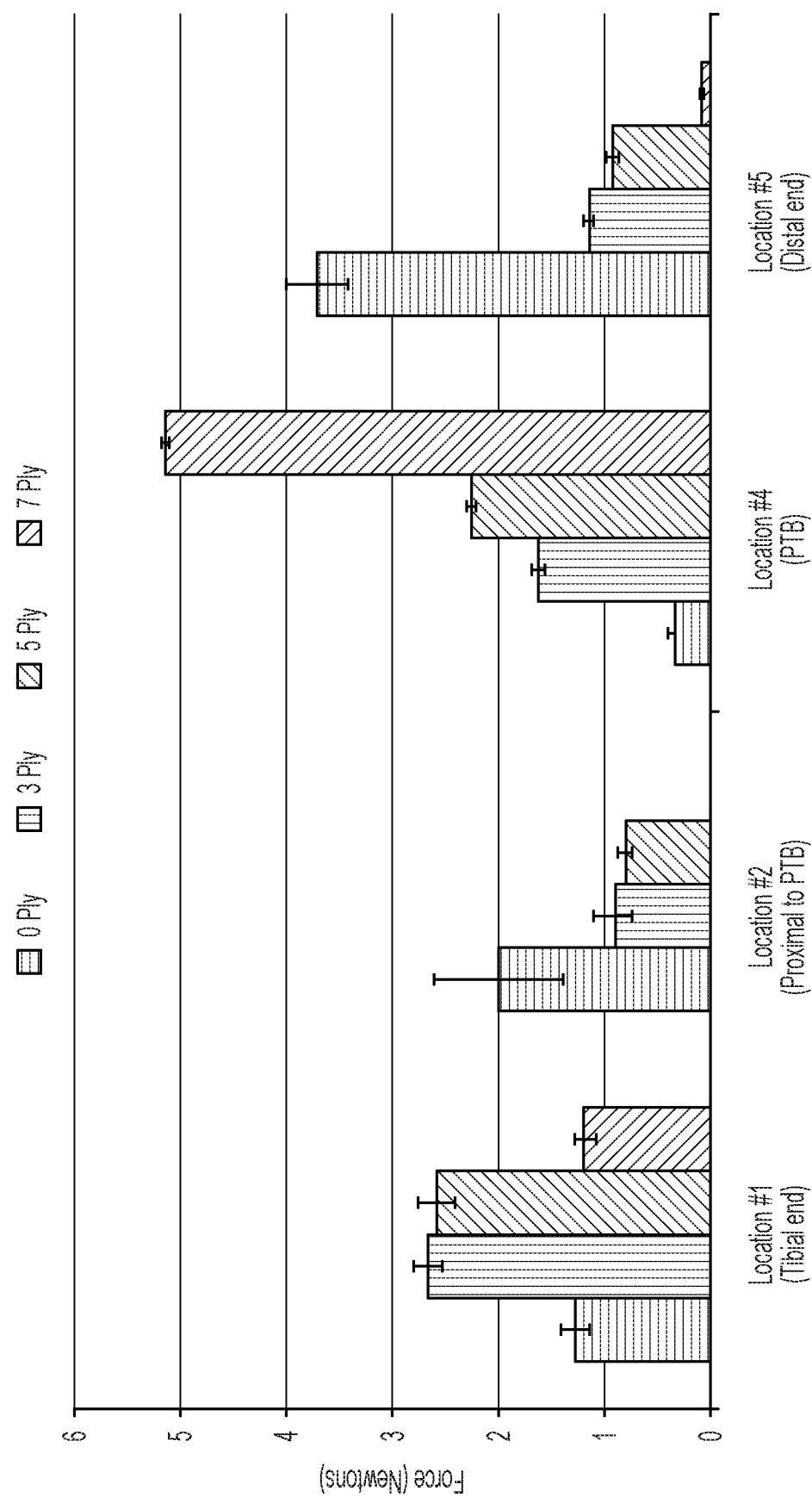
FIG. 3D shows a graph of the results of simulated standing tests.

Determining sensor location. To determine where to place pressure sensors on a prosthetic socket to best classify socket fit, simulated standing tests were performed using a silicone residual limb model (FIG. 3A). A socket was fabricated to fit the residual limb model with a 5-ply sock. A thin force sensor (i.e., from Tekscan FlexiForce) was placed in four different locations within the socket sensitive to different sock levels (FIGS. 3B and 3C). Then 100 pounds of static force was applied to the socket to simulate standing, and the simulated standing test was repeated for three trials each of four different sock conditions (no socks, 3-ply, 5-ply, and 7-ply) while recording forces at the four sensor locations. Results showed two sensor locations that can correctly and repeatedly distinguish the different sock conditions were the patellar tendon bar (PTB) and the distal end of the socket (FIG. 3D). The distal end sensor location was chosen for the disclosed system because it would be easier to build space for the system hardware in the distal end of the socket than around the PTB. Additionally, it is contemplated that a pressure sensor at the distal end of the socket can improve upon an established clinical procedure, for example, where a prosthetist can put clay at the bottom of the socket and examines the clay's deformation to assess socket fit.

After testing several types of pressure sensing systems during walking and standing, the system disclosed herein was implemented and can use a commercial, off-the-shelf pressure transducer in a custom-designed enclosure (FIGS. 4A and 4B) as disclosed further herein. The disclosed sensor assembly 100 can be designed to have the same form factor as a shuttle lock (at the distal end of a lower limb socket (FIGS. 4A-4D) and to be easy for a prosthetist to build into a prosthetic socket. The system disclosed herein can detect motion of the residual limb relative to the prosthetic socket. As further disclosed herein, the motion can be detected pneumatically through a membrane which is in contact with the distal end of the residual limb. Further, the disclosed system design can include processing circuitry that is capable of alerting the prosthesis user when there is a poor fit, and ensuring that wired connections to external hardware are not singly relied upon to process the sensor signals (FIG. 4E).

Figure 5A:
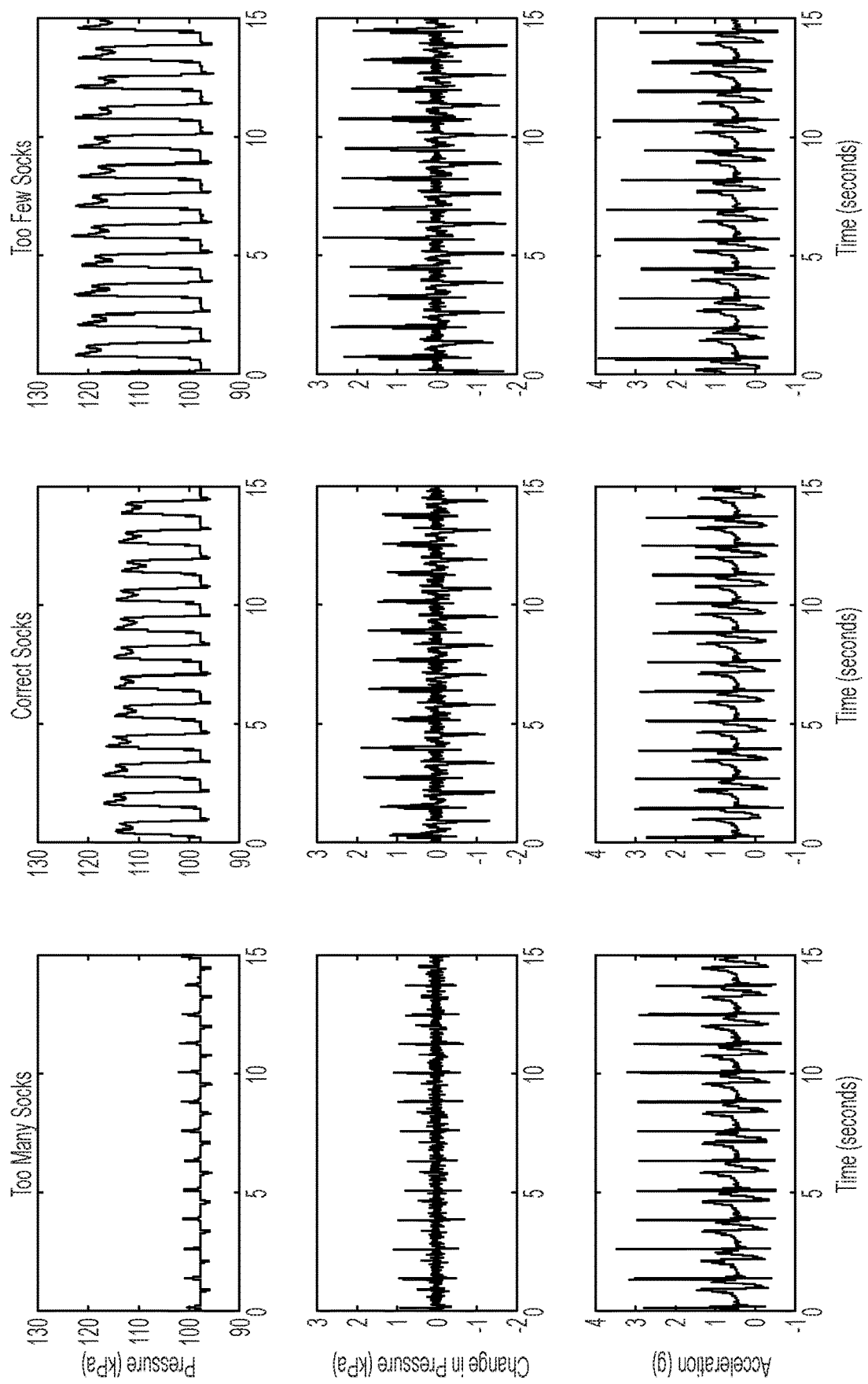
FIGS. 5A-B shows graphs of the results of the three sock conditions during walking.
Figure 5B:
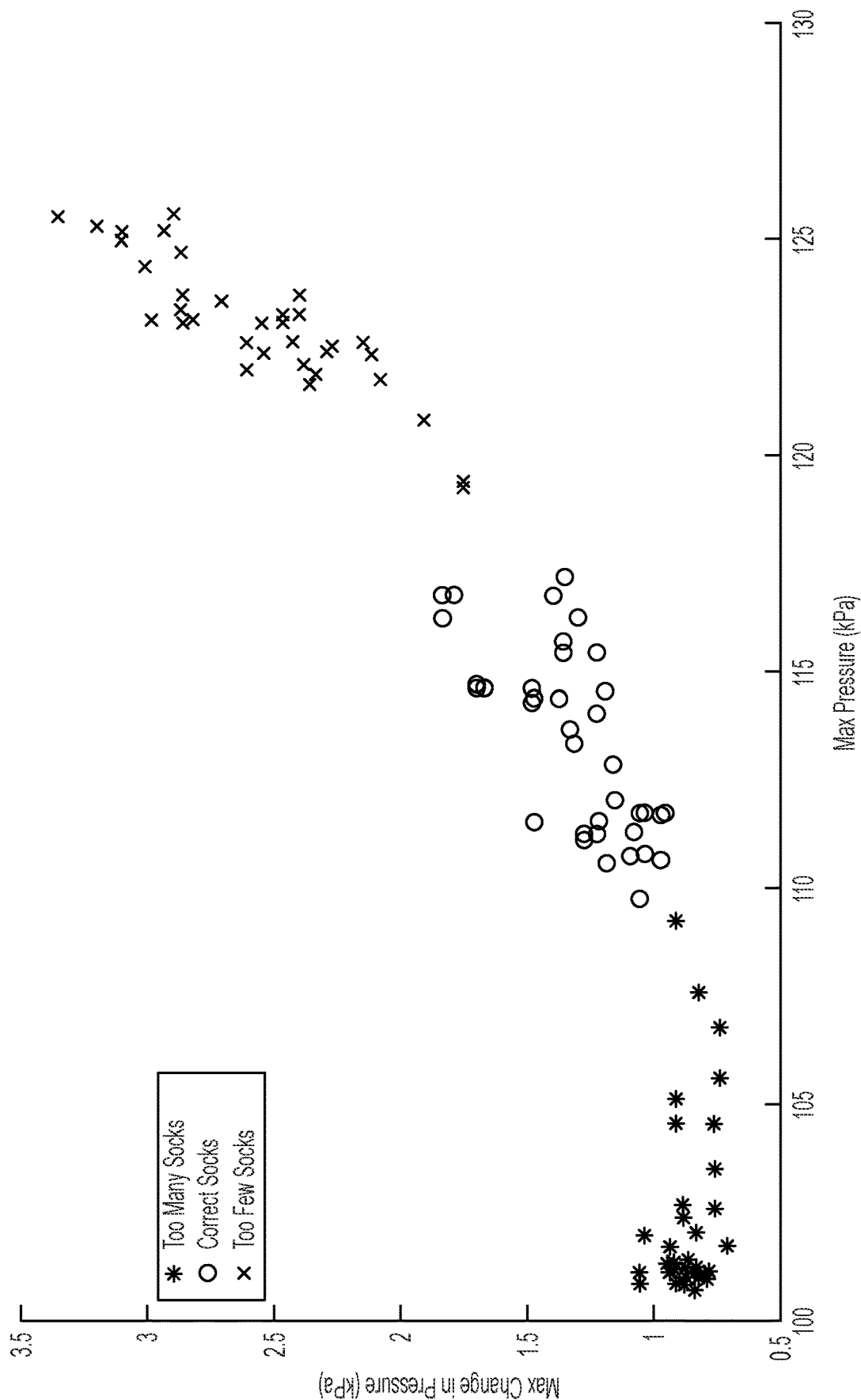

The system disclosed herein was tested on a subject who has a transtibial amputation and is an experienced prosthesis user. As part of the testing protocol, distal-end pressure and accelerometer data was recorded while the subject walked for 15 second trials for each of three different sock conditions: correct socks for a good socket fit (6-ply), too few socks (3-ply), and too many socks (9-ply). Three walking trials were performed to assess repeatability. Because the subject stated that he felt his limb piston (slide) both more and faster in the socket, peak pressures and the rate of pressure fluctuations were reviewed (FIG. 5A shows representative data). The accelerometer data coincided with the pistoning (sliding) and clearly showed that the subject was walking as opposed to sitting, standing, or swaying. When the max pressure and max change in pressure was analyzed for each two-second gait cycle, results showed that the pressure sensor data was able to differentiate the sock conditions during walking (FIG. 5B). It is contemplated that different socket-fit detection algorithms in participants that are learning to use a prosthesis in their post-amputation rehabilitation care can be tested.

Evaluating Sufficiency of System Alerts. In another example, experienced prosthesis users using a socket-fit sensor system providing user-observable outputs for half a day can be assessed on visual and vibrotactile feedback elements to confirm that the alerts generated by the system when wearing different levels of socks are sensed without being too loud or socially unacceptable. Pressure and accelerometer data can be collected and used to refine socket-fit detection algorithms. The socket-fit sensor system can be produced for in-clinic testing.

Testing and Modification of the System. The socket-fit sensor system can be tested using patients during their post-amputation rehabilitation care. The subjects can use their prosthetic socket as per their usual clinical care pathway. However, the system disclosed herein can be fabricated in the distal end of their prosthetic socket. The prosthetic sockets can be fabricated using standard techniques and material such that if the socket-fit sensor system breaks or fails, the function and safety of the prosthesis will not be impacted.

Patients with transtibial amputations typically undergo two weeks of in-clinic, prosthesis training. First, a prosthetist fabricates a test socket and assesses the fit visually or using a clay ball test. The prosthetist then educates the patient on sock management, including how the socket feels with too many, too few, and the correct number of socks. Next, the patient sees a PT for twice-daily, 30-minute therapy sessions. As the patient progresses, they are instructed by the PT to wear the prosthesis outside of therapy for increasingly longer periods until they are up to 4 to 6 hours of total (not necessarily continuous) wear time per day at discharge. It is not uncommon for patients to develop pain or discomfort when using the prosthesis on their own, necessitating re-training on sock management. The prosthetists and PTs may repeat training and education on sock management as necessary throughout the patients' rehabilitation. This clinical progression can vary for each patient.

In-clinic testing of the disclosed system can be integrated with the subject's normal clinical care progression. The subjects can use the socket-fit sensor system anytime they use their prosthesis, including during the initial socket fitting with the prosthetist, twice daily physical therapy sessions, training and education sessions as needed, and prosthesis use outside of therapy. The system can detect walking movements from the accelerometer and record pressure and acceleration data.

When the socket-fit detection algorithm is turned on by a clinician and detects poor socket fit, the processing circuitry of the system can alert the subject using visual and vibrotactile feedback. To train the socket-fit detection algorithm, the subject can walk while wearing too many, too few, and correct socks and then "label" the data by selecting the appropriate button on the clinician interface. The clinician interface can also be used to turn on/off the alert system and change settings for the visual and vibrotactile feedback. The PT or prosthetist can update or re-train the algorithm at any time. Socket fit, residual limb circumference, and socket comfort will be measured by the prosthetist or PT at the beginning of each session with the subject and will occur at least twice daily during the approximately two-week rehabilitation period. Before discharge, unstructured interviews will be performed with the subjects to assess their satisfaction with the socket-fit sensor system, their self-efficacy and engagement in sock management, and their interest in using the system in a home environment after discharge.

The data from the in-clinic tests can be used to assess the socket-fit sensor system disclosed herein. Based on feedback from the subjects and clinicians, the alert system can be designed to ensure it effectively informs subjects about needing to add or remove socks. The accuracy of the socket-fit detection algorithm can be assessed for each subject by comparing the pressure-based alert data with twice-daily clinician fit assessments. For the algorithm, a linear support vector machine can be used to classify the labeled data ("too many socks" versus "too few socks" versus "correct socks"). If the classifier accuracy is low (perhaps because of incomplete labeling of the data), naive Bayes classifiers, k-nearest neighbors classifiers, nonlinear support vector machines, and boosting/bagging methods, and combinations thereof, can be employed. It is contemplated that algorithms can be developed and tested. The pressure and accelerometer data, comfort scores, and limb circumference measures can be analyzed to assess how the algorithm adapts to individual subject differences in anatomy, function, and limb-volume fluctuations.

In use, it is contemplated that the system disclosed herein may have several benefits to subjects, including, veterans during rehabilitation from lower-limb amputation. It is contemplated that the disclosed socket-fit sensor system can provide subjects with an easy-to-use tool to self-manage prosthetic socket fit. Enhanced education and training of effective socket management immediately following an amputation can boost self-efficacy and engagement in self-care and can reduce preventable pain, discomfort, and skin issues. This training can be important to subjects at an early stage in their rehabilitation as they establish self-management habits and strategies.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1. A sensor assembly comprising:
a rigid body defining an opening extending through a thickness of the rigid body;
a pressure sensor positioned in fluid communication with the opening of the rigid body; and
a membrane positioned in overlying relation to the rigid body,
wherein the rigid body, a lower surface of the membrane, and the pressure sensor cooperate to define at least a portion of a chamber configured to receive a fluid,
wherein the membrane has an upper surface that is configured for contact with a distal portion of a residual limb of a patient,
wherein the sensor assembly is configured for complementary receipt within a distal portion of a prosthetic socket, and
wherein the sensor is configured to produce an output indicative of changes in pressure within the chamber in response to deformation of the membrane by the distal portion of the residual limb of the patient.

Aspect 2. The sensor assembly of aspect 1, further comprising a lower body that supports the pressure sensor in an operative position and is secured to the rigid body.

Aspect 3. The sensor assembly of aspect 2, wherein in the operative position, a portion of the pressure sensor is received within the chamber, and wherein the sensor assembly further comprises a sealing element that forms a seal between the pressure sensor and the rigid body.

Aspect 4. The sensor assembly of aspect 3, wherein the sealing element is an O-ring.

Aspect 5. The sensor assembly of any one of aspects 2-4, wherein the membrane is secured to the rigid body.

Aspect 6. The sensor assembly of aspect 5, wherein the rigid body has a peripheral edge, and wherein the membrane has a peripheral edge portion that covers at least a portion of the peripheral edge of the rigid body.

Aspect 7. The sensor assembly of aspect 6, further comprising a retaining ring that overlies at least a portion of the peripheral edge portion of the membrane and is secured to the rigid body to retain the membrane in overlying relation to the rigid body.

Aspect 8. The sensor assembly of any one of aspects 6-7, wherein the rigid body has an upper body portion and a lower body portion that is inwardly recessed from, and that has a decreased diameter relative to, the upper body portion, and wherein the upper body portion comprises a circumferential flange that defines the peripheral edge of the rigid body.

Aspect 9. The sensor assembly of aspect 8, wherein the circumferential flange of the upper body portion has a lower surface extending between the lower body portion and the peripheral edge of the rigid body, wherein at least a portion of the peripheral edge portion of the membrane engages the lower surface of the circumferential flange.

Aspect 10. The sensor assembly of aspect 9, further comprising a retaining ring that secures the membrane to the lower surface of the circumferential flange of the upper body portion of the rigid body.

Aspect 11. The sensor assembly of any one of aspects 8-10, wherein the membrane is molded with an undercut portion that is complementary to the shape of the circumferential flange of the upper body portion of the rigid body.

Aspect 12. The sensor assembly of aspect 11, wherein the peripheral edge portion of the molded membrane defines a circumferential projection that is configured to frictionally engage a portion of the lower body.

Aspect 13. The sensor assembly of any one of aspects 2-12, further comprising processing circuitry that is communicatively coupled to the pressure sensor.

Aspect 14. The sensor assembly of aspect 13, wherein the lower body has an upper surface that defines a first receptacle that receives and supports the pressure sensor in the operative position, and wherein the lower body has a lower surface that defines a second receptacle that is configured to receive at least a portion of the processing circuitry.

Aspect 15. The sensor assembly of aspect 13 or aspect 14, further comprising an accelerometer or a gyroscope that is communicatively coupled to the processing circuitry.

Aspect 16. A socket fit management system comprising: a prosthetic socket having a distal portion; and a sensor assembly (optionally, a sensor assembly of any one of the preceding aspects), wherein the sensor assembly is received within the distal portion of the prosthetic socket.

Aspect 17. The socket fit management system of aspect 16, wherein the sensor assembly comprises processing circuitry communicatively coupled to the pressure sensor.

Aspect 18. The socket fit management system of aspect 17, further comprising a remote computing device that is communicatively coupled to the processing circuitry of the sensor assembly.

Aspect 19. The socket fit management system of aspect 18, wherein the sensor assembly further comprises an accelerometer or a gyroscope that is communicatively coupled to the processing circuitry of the sensor assembly.

Aspect 20. A method comprising:
using the socket fit management system of any one of aspects 16-19;
measure changes in pressure resulting from movement of a residual limb having a distal portion in contact with an upper surface of the membrane of the sensor assembly.

Aspect 21. The method of aspect 20, wherein the sensor assembly comprises processing circuitry communicatively coupled to the pressure sensor, and wherein the processing circuitry is configured to determine a quality of fit between the residual limb and a socket within which the sensor assembly is positioned.

Aspect 22. The method of aspect 21, further comprising remotely transmitting data indicative of the quality of fit between the residual limb and the socket from the processing circuitry of the sensor assembly to a remote computing device.

Aspect 23. The method of aspect 22, wherein the sensor assembly further comprises an accelerometer or a gyroscope that is communicatively coupled to the processing circuitry of the sensor assembly, wherein the accelerometer or gyroscope produces an output indicative of a type of movement of the patient.

What is claimed is:

1. A sensor assembly comprising:
    a rigid body defining an opening extending through a thickness of the rigid body;
    a pressure sensor positioned in fluid communication with the opening of the rigid body;
    a sealing element that forms a seal between portions of the pressure sensor and portions of the rigid body that define the opening; and
    a membrane positioned in overlying relation to the rigid body, wherein the membrane is sealed to the rigid body,
    wherein the rigid body, a lower surface of the membrane, the pressure sensor, and the sealing element cooperate to define at least a portion of a sealed chamber that contains a fluid,
    wherein the membrane has an upper surface that is configured for contact with a distal portion of a residual limb of a patient,
    wherein the sensor assembly is configured for complementary receipt within a distal portion of a prosthetic socket, and
    wherein the pressure sensor is configured to produce an output indicative of changes in pressure within the sealed chamber in response to deformation of the membrane by the distal portion of the residual limb of the patient.

2. The sensor assembly of claim 1, further comprising a lower body that supports the pressure sensor in an operative position and is secured to the rigid body.

3. The sensor assembly of claim 2, wherein in the operative position, a portion of the pressure sensor is positioned outside the sealed chamber.

4. The sensor assembly of claim 1, wherein the sealing element is an O-ring that surrounds a portion of the pressure sensor.

5. The sensor assembly of claim 1, wherein the membrane is secured to the rigid body.

6. The sensor assembly of claim 5, wherein the rigid body has a peripheral edge, and wherein the membrane has a peripheral edge portion that covers at least a portion of the peripheral edge of the rigid body.

7. The sensor assembly of claim 6, further comprising a retaining ring that overlies at least a portion of the peripheral edge portion of the membrane and is secured to the rigid body to retain the membrane in overlying relation to the rigid body.

8. The sensor assembly of claim 6, wherein the rigid body has an upper body portion and a lower body portion that is inwardly recessed from, and that has a decreased diameter relative to, the upper body portion, and wherein the upper body portion comprises a circumferential flange that defines the peripheral edge of the rigid body.

9. The sensor assembly of claim 8, wherein the circumferential flange of the upper body portion has a lower surface extending between the lower body portion and the peripheral edge of the rigid body, wherein at least a portion of the peripheral edge portion of the membrane engages the lower surface of the circumferential flange.

10. The sensor assembly of claim 9, further comprising a retaining ring that secures the membrane to the lower surface of the circumferential flange of the upper body portion of the rigid body.

11. The sensor assembly of claim 8, wherein the membrane is molded with an undercut portion that is complementary to the shape of the circumferential flange of the upper body portion of the rigid body.

12. The sensor assembly of claim 11, wherein the peripheral edge portion of the molded membrane defines a circumferential projection that is configured to frictionally engage a portion of the lower body.

13. The sensor assembly of claim 2, further comprising processing circuitry that is communicatively coupled to the pressure sensor.

14. The sensor assembly of claim 13, wherein the lower body has an upper surface that defines a first receptacle that receives and supports the pressure sensor in the operative position, and wherein the lower body has a lower surface that defines a second receptacle that is configured to receive at least a portion of the processing circuitry.

15. The sensor assembly of claim 13, further comprising an accelerometer or a gyroscope that is communicatively coupled to the processing circuitry.

16. A socket fit management system comprising:
a prosthetic socket having a distal portion; and
a sensor assembly of claim 1, wherein the sensor assembly is received within the distal portion of the prosthetic socket.

17. The socket fit management system of claim 16, wherein the sensor assembly comprises processing circuitry communicatively coupled to the pressure sensor.

18. The socket fit management system of claim 17, further comprising a remote computing device that is communicatively coupled to the processing circuitry of the sensor assembly.

19. The socket fit management system of claim 18, wherein the sensor assembly further comprises an accelerometer or a gyroscope that is communicatively coupled to the processing circuitry of the sensor assembly.

20. A method comprising:
using a sensor assembly of claim 1, wherein the sensor assembly is received within a distal portion of a prosthetic socket; and
measuring changes in pressure resulting from movement of a residual limb having a distal portion in contact with an upper surface of the membrane of the sensor assembly.

21. The method of claim 20, wherein the sensor assembly comprises processing circuitry communicatively coupled to the pressure sensor, and wherein the processing circuitry is configured to determine a quality of fit between the residual limb and a socket within which the sensor assembly is positioned.

22. The method of claim 21, further comprising remotely transmitting data indicative of the quality of fit between the residual limb and the socket from the processing circuitry of the sensor assembly to a remote computing device.

23. The method of claim 22, wherein the sensor assembly further comprises an accelerometer or a gyroscope that is communicatively coupled to the processing circuitry of the sensor assembly, wherein the accelerometer or gyroscope produces an output indicative of a type of movement of the patient.

24. A sensor assembly comprising:
a rigid body defining an opening extending through a thickness of the rigid body;
a pressure sensor positioned in fluid communication with the opening of the rigid body;
a membrane positioned in overlying relation to the rigid body; and
a lower body that supports the pressure sensor in an operative position and is secured to the rigid body,
wherein the rigid body, a lower surface of the membrane, and the pressure sensor cooperate to define at least a portion of a chamber configured to receive a fluid,
wherein the membrane has an upper surface that is configured for contact with a distal portion of a residual limb of a patient,
wherein the sensor assembly is configured for complementary receipt within a distal portion of a prosthetic socket, and
wherein the pressure sensor is configured to produce an output indicative of changes in pressure within the sealed chamber in response to deformation of the membrane by the distal portion of the residual limb of the patient,
wherein the membrane is secured to the rigid body, wherein the rigid body has a peripheral edge, and wherein the membrane has a peripheral edge portion that covers at least a portion of the peripheral edge of the rigid body, and wherein the rigid body has an upper body portion and a lower body portion that is inwardly recessed from, and that has a decreased diameter relative to, the upper body portion, and wherein the upper body portion comprises a circumferential flange that defines the peripheral edge of the rigid body.

* * * * *